(12) United States Patent
Freeman et al.

(10) Patent No.: US 7,038,013 B2
(45) Date of Patent: May 2, 2006

(54) B7-4 POLYPEPTIDES AND USES THEREFOR

(75) Inventors: Gordon Freeman, Brookline, MA (US); Vassiliki Boussiotis, Brookline, MA (US); Tatyana Chernova, Brighton, MA (US); Nelly Malenkovich, Boston, MA (US)

(73) Assignee: Dana-Faber Cancer Institute, Inc., Boston, MA (US)

( * ) Notice: Subject to any disclaimer, the term of this patent is extended or adjusted under 35 U.S.C. 154(b) by 272 days.

(21) Appl. No.: 10/002,775

(22) Filed: Nov. 2, 2001

(65) Prior Publication Data

US 2002/0102651 A1 Aug. 1, 2002

Related U.S. Application Data

(62) Division of application No. 09/644,934, filed on Aug. 23, 2000, now Pat. No. 6,936,704.

(60) Provisional application No. 60/150,390, filed on Aug. 23, 1999.

(51) Int. Cl.
*C07K 14/47* (2006.01)
*C07K 14/725* (2006.01)
*C07K 16/46* (2006.01)
*A61K 38/17* (2006.01)
*A61K 39/395* (2006.01)

(52) U.S. Cl. .................. 530/350; 530/351; 530/387.3; 514/12; 514/21; 424/134.1

(58) Field of Classification Search ................ 530/350, 530/351, 387.3
See application file for complete search history.

(56) References Cited

FOREIGN PATENT DOCUMENTS

WO  WO 95/03408  2/1995

OTHER PUBLICATIONS

Attwood, Teresa K. "The Babel of Bioinformatics" *Science* 290(5491):471-473 (Oct. 27, 2000).
Coyle, Anthony J. et al. "The expanding B7 superfamily: Increasing complexity in costimulatory signals regulating T cell function" *Nature Immunology* 2(3):203-209 (Mar. 2001).
Dong, Haidong et al. Genbank Acession No. AF177937 Homo sapiens B7-H1 mRNA, complete cds (Jan. 19, 2000).
Dong, Haidong et al. "B7-H1, a third member of the B7 family, co-stimulates T-cell proliferation and interleukin-10 secretion" *Nature Medicine* 5(12): 1365-1369 (1999).
Freeman, Gordon J. et al. "Engagement of the PD-1 Immunoinhibitory Recpetor by a Novel B7 Family Member Leads to Negative Regulation of Lymphocyte Activation" *Journal of Experimental Medicine* 192(7):1027-1034 (1998).
Henry, Joelle et al. "Structure and evolution of the extended B7 family" *Immunology Today* 20(6):285-288 (1999).
Skolnick, Jeffrey et al. "From genes to protein structure and function: novel applications of computational approaches in the genomic era" *Trends In Biotechnology* 18(1):34-39 (Jan. 2000).
*Steadman's Medical Dictionary*, 24th edition, 1982 Williams & Wilkins, Baltimore, MD, USA, p. 42.
Voet, Donald et al. *Biochemistry* vol. 1, 1990 John Wiley & Sons, pp. 126-128, 230.
Genbank Acession No. AA292201 zt50f01.r1 Soares ovary tumor NbHOT *Homo sapiens* cDNA clone IMAGE:725785 5', mRNA sequence (Apr. 21, 1997).
Genbank Acession No. AA399416 zt50f01.s1 Soares ovary tumor NbHOT *Homo sapiens* cDNA clone IMAGE:725785 3', mRNA sequence (Apr. 29, 1997).
Genbank Acession No. Q13410 Butyrophilin precursor (BT) (Nov. 1, 1997).

*Primary Examiner*—Phillip Gambel
*Assistant Examiner*—Ilia Ouspenski
(74) *Attorney, Agent, or Firm*—Foley Hoag LLP

(57) ABSTRACT

The invention provides isolated nucleic acids molecules, designated B7-4 nucleic acid molecules, which encode novel B7-4 polypeptides. The invention also provides antisense nucleic acid molecules, recombinant expression vectors containing B7-4 nucleic acid molecules, host cells into which the expression vectors have been introduced, and nonhuman transgenic animals in which a B7-4 gene has been introduced or disrupted. The invention still further provides isolated B7-4 proteins, fusion proteins, antigenic peptides and anti-B7-4 antibodies. Diagnostic, screening, and therapeutic methods utilizing compositions of the invention are also provided.

14 Claims, 12 Drawing Sheets

FIG. 1

```
GCTTCCGGAGGCTCCGACCAGCCGCGCTTCTGTCGCCTGCAGGGCATTCCA
GAAAGATGAGGATATATTGCTGTCTTTATTCATGACCTACTGGCATTGCTG
AACGCATTACTGTCACGGTTCCCAAGGACCTATATGTGTAGAGTATGGTA
GCAATATGACAATTGAATGCAAATTCCCAGTAGAAACAATTAGACCTGGC
TGCACTACTAATTGTCTATTGGGAAATGGAGGATAAGAACATTATTCAATTGTGC
ATGGAGGAAGACCTGAAGGTTCAGCATAGTAGCTACAGACAGAGGGCCC
GGCTGTTGAAGGACCAGCTCTCCCTGGGAAATGCTGCACTTCAGATCACAGA
TGTGAAATTGCAGGATGCAGGGGTGTACCGCTGCATGATCAGTATGGT
GCCGACTACAAGCGAATTACTGTGAAAGTCACCCATACAACAAAATCA
ACCAAAGAATTTGGTTGTGTGGATCCAGTCACCTCTGAACATGAACATGT
CAGGCTGAGGGCTACCCCCAAGGCCGAAGTCATCTGGACAAGCAGTGACCATC
AAGTCCTGAGTGGTAAGACCACCACCAATTCAACACAACAACTAATGAGATTT
TTTCAATGTGACCAGCAGCACACTGAGAATCAACAACAACAACTAATGAGATTT
CTACTGCACTTTAGGAGATTAGATCCTGAATGTGTCATTAATATGTCTAACACTGTC
GTCATCCCCAGTAATATTCTGAATGTGTCCTATCATGATCAGTGATTGTTGAA
CCCTAGCACCTAGCATGATGTCTGCCTATCATGATCAGTGATTGTTGAA
TAAATGAATGAATGAATAACACTATGTTACTTACTTAAAATATATCCTAATTCCTCAC
CTCCATTCATCCAAACCATATTGTTACTTAATAAACATTCAGCAGATATTAT
GGAATAAAAAAAAAAAAAAAAAA
```

FIG. 2

```
CGAGGCTCCGCACCAGCCGCGCTTCTGTCCGCCTGCAGGGCATTCCAGAAAGA
TGAGGATATTTGCTGTCTTTATATTCATGACCTACTGGCATTTGCTGAACGCATT
TACTGTCACGGTTCCCAAGGACCTATATGTGGTAGAGTATGGTAGCAATATGAC
AATTGAATGCAAATTCCCAGTAGAAAAACAATTAGACCTGGCTGCACTAATTGT
CTATTGGGAAATGGAGGATAAGAACATTATTCAATTTGTGCATGGAGAGGAAG
ACCTGAAGGTTCAGCATAGTAGCTACAGACAGAGGGCCCGGCTGTTGAAGGAC
CAGCTCTCCCTGGGAAATGCTGCACTTCAGATCACAGATGTGAAATTGCAGGAT
GCAGGGGTGTACCGCTGCATGATCAGCTATGGTGGTGCCGACTACAAGCGAAT
TACTGTGAAAGTCAATGCCCCATACAACAAAATCAACCAAAGAATTTTGGTTGT
GGATCCAGTCACCTCTGAACATGAACTGACATGTCAGGCTGAGGGCTACCCCA
AGGCCGAAGTCATCTGGACAAGCAGTGACCATCAAGTCCTGAGTGGTAAGACC
ACCACCACCAATTCCAAGAGAGAGGAGAAGCTTTTCAATGTGACCAGCACACT
GAGAATCAACACAACAACTAATGAGATTTTCTACTGCACTTTTAGGAGATTAGA
TCCTGAGGAAAACCATACAGCTGAATTGGTCATCCCAGAACTACCTCTGGCACA
TCCTCCAAATGAAAGGACTCACTTGGTAATTCTGGGAGCCATCTTATTATGCCTT
GGTGTAGCACTGACATTCATCTTCCGTTTAAGAAAAGGGAGAATGATGGATGT
GAAAAAATGTGGCATCCAAGATACAAACTCAAAGAAGCAAAGTGATACACATTT
GGAGGAGACGTAATCCAGCATTGGAACTTCTGATCTTCAAGCAGGGATTCTCA
ACCTGTGGTTTAGGGGTTCATCGGGGCTGAGCGTGACAAGAGGAAGGAATGG
GCCCGTGGGATGCAGGCAATGTGGGACTTAAAAGGCCCAAGCACTGAAAATG
GAACCTGGCGAAAGCAGAGGAGGAGAATGAAGAAAGATGGAGTCAAACAGGG
AGCCTGGAGGGAGACCTTGATACTTTCAAATGCCTGAGGGGCTCATCGACGCC
TGTGACAGGGAGAAAGGATACTTCTGAACAAGGAGCCTCCAAGCAAATCATCC
ATTGCTCATCCTAGGAAGACGGGTTGAGAATCCCTAATTTGAGGGTCAGTTCCT
GCAGAAGTGCCCTTTGCCTCCACTCAATGCCTCAATTTGTTTTCTGCATGACTGA
GAGTCTCAGTGTTGGAACGGGACAGTATTTATGTATGAGTTTTTCCTATTTATTT
TGAGTCTGTGAGGTCTTCTTGTCATGTGAGTGTGGTTGTGAATGATTTCTTTTGA
AGATATATTGTAGTAGATGTTACAATTTTGTCGCCAAACTAAACTTGCTGCTTAA
TGATTTGCTCACATCTAGTAAAACATGGAGTATTTGTAAAAAAAAAAAAAAAA
```

FIG. 3

292 secreted (245 amino acids)

Signal/IgV/IgC/hydrophilic tail
 (a)     (b)  (c)       (d)
Ig cysteines in large bold MRIFAVFIFMTYWHLLNA  (signal)

FTVTVPKDLYVVEYGSNMTIECKFPVEKQLDLAALIVYWEMEDKN
IIQFVHGEEDLKVQHSSYRQRARLLKDQLSLGNAALQITDVKLQD
AGVYRCMISYGGADYKRITVKVNAPY  (IgV)

NKINQRILVVDPVTSEHELTCQAEGYPKAEVIWTSSDHQVLSGKT
TTTNSKREEKLFNVTSTLRINTTTNEIFYCTFRRLDPEENHTAEL
VIP  (IgC)

GNILNVSIKICLTLSPST  (hydrophilic tail)

FIG. 4

292 membrane   (290 amino acids)

Signal/IgV/IgC/transmembrane (underlined) plus cytoplasmic

Ig cysteines in large bold

MRIFAVFIFMTYWHLLNA   (signal)

FTVTVPKDLYVVEYGSNMTIECKFPVEKQLDLAALIVYWEMEDKN
IIQFVHGEEDLKVQHSSYRQRARLLKDQLSLGNAALQITDVKLQD
AGVYRCMISYGGADYKRITVKVNAPY   (IgV)

NKINQRILVVDPVTSEHELTCQAEGYPKAEVIWTSSDHQVLSGKT
TTTNSKREEKLFNVTSTLRINTTTNEIFYCTFRRLDPEENHTAEL
VIP   (IgC)

ELPLAHPPNER<u>THLVILGAILLCLGVALTFIF</u>RLRKGRMMDVKKC
GIQDTNSKKQSDTHLEET   (transmembrane plus cytoplasmic)

FIG. 5A

```
AGATAGTTCCCAAAACATGAGGATATTTGCTGGCATTATATTCACAGCCTGC
TGTCACTTGCTACGGGCGTTTACTATCACGGCTCCAAAGGACTTGTACGTG
GTGGAGTATGGCAGCAACGTCACGATGGAGTGCAGATTCCCTGTAGAACG
GGAGCTGGACCTGCTTGCGTTAGTGGTGTACTGGGAAAAGGAAGATGAGC
AAGTGATTCAGTTTGTGGCAGGAGAGGAGGACCTTAAGCCTCAGCACAGCA
ACTTCAGGGGGAGAGCCTCGCTGCCAAAGGACCAGCTTTTGAAGGGAAAT
GCTGCCCTTCAGATCACAGACGTCAAGCTGCAGGACGCAGGCGTTTACTGC
TGCATAATCAGCTACGGTGGTGCGGACTACAAGCGAATCACGCTGAAAGTC
AATGCCCCATACCGCAAAATCAACCAGAGAATTTCCGTGGATCCAGCCACTT
CTGAGCATGAACTAATATGTCAGGCCGAGGGTTATCCAGAAGCTGAGGTAA
TCTGGACAAACAGTGACCACCAACCCGTGAGTGGGAAGAGAAGTGTCACCA
CTTCCCGGACAGAGGGGATGCTTCTCAATGTGACCAGCAGTCTGAGGGTCA
ACGCCACAGCGAATGATGTTTTCTACTGTACGTTTTGGAGATCACAGCCAG
GGCAAAACCACACAGCGGAGCTGATCATCCAGAACTGCCTGCAACACATC
CTCCACAGAACAGGACTCACTGGGTGCTTCTGGGATCCATCCTGTTGTTCC
TCATTGTAGTGTCCACGGTCCTCCTCTTCTTGAGAAAACAAGTGAGAATGCT
AGATGTGGAGAAATGTGGCGTTGAAGATACAAGCTCAAAAAACCGAAATGA
TACACAATTCGAGGAGACGTAAGCAGTGTTGAACCCTCTGATCGTCGATTG
GCAGCTTGTGGTCTGTGAAAGAAAGGGCCCATGGGACATGAGTCCAAAGAC
TCAAGATGGAACCTGAGGGAGAGAACCAAGAAAGTGTTGGGAGAGGAGCC
TGGAACAACGGACATTTTTTCCAGGGAGACACTGCTAAGCAAGTTGCCCAT
CAGTCGTCTTGGGAAATGGATTGAGGGTTCCTGGCTTAGCAGCTGGTCCTT
GCACAGTGACCTTTTCCTCTGCTCAGTGCCGGGATGAGAGATGGAGTCATG
AGTGTTGAAGAATAAGTGCCTTCTATTTATTTTGAGTCTGTGTGTTCTCACTT
TGGGCATGTAATTATGACTGGTGAATTCTGACGACATGATAGATCTTAAGAT
GTAGTCACCAAACTCAACTGCTGCTTAGCATCCTCCGTAACTACTGATACAA
GCAGGGAACACAGAGGTCACCTGCTTGGTTTGACAGGCTCTTGCTGTCTGA
CTCAAATAATCTTTATTTTTCAGTCCTCAAGGCTCTTCGATAGCAGTTGTTCT
GTATCAGCCTTATAGGTGTCAGGTATAGCACTCAACATCTCATCTCATTACA
ATAGCAACCCTCATCACCATAGCAACAGCTAACCTCTGTTATCCTCACTTCA
TAGCCAGGAAGCTGAGCGACTAAGTCACTTGCCCACAGAGTATCAGCTCTC
AGATTTCTGTTCTTCAGCCACTGTCCTTTCAGGATAGAATTTGTCGTTAAGAA
ATTAATTTAAAAACTGATTATTGAGTAGCATTGTATATCAATCACAACATGCC
TTGTGCACTGTGCTGGCCTCTGAGCATAAAGATGTACGCCGGAGTACCGGT
CGGACATGTTTATGTGTGTTAAATACTCAGAGAAATGTTCATTAACAAGGAG
CTTGCATTTTAGAGACACTGGAAAGTAACTCCAGTTCATTGTCTAGCATTAC
ATTTACCTCATTTGCTATCCTTGCCATACAGTCTCTTGTTCTCCATGAAGTGT
CATGAATCTTGTTGAATAGTTCTTTTATTTTTTAAATGTTTCTATTTAAATGATA
TTGACATCTGAGGCGATAGCTCAGTTGGTAAAACCCTTTCCTCACAAGTGTG
AAACCCTGAGTCTTATCCCTAGAACCCACATAAAAAACAGTTGCGTATGTTT
GTGCATGCTTTTGATCCCAGCACTAGGGAGGCAGAGGCAGGCAGATCCTG
AGCTCTCATTGACCACCCAGCCTAGCCTACATGGTTAGCTCCAGGCCTACA
GGAGCTGGCAGAGCCTGAAAAACGATGCCTAGACACACACACACACACACA
CACACACACACACACACACACACCATGTACTCATAGACCTAAGTGCACC
CTCCTACACATGCACACACATACAATTCAAACACAAATCAACAGGGAATTGT
```

FIG. 5B

```
CTCAGAATGGTCCCCAAGACAAAGAAGAAGAAAAACACCAAACCAGCTCTA
TTCCCTCAGCCTATCCTCTCTACTCCTTCCTAGAAGCAACTACTATTGTTTTT
GTATATAAATTTACCCAACGACAGTTAATATGTAGAATATATATTAAAGTGTC
TGTCAATATATATTATCTCTTTCTTTCTTTCTTCCTTTCTTTCTTTCTTTC
TTTCTTTCTTTCTTTCTTTCTTTCTTTCTTCCTTCCTTCCTTCCTTCCTTC
CTTCCTTCCTTCCTTTCTTTCTTTCTTTCTTTTTTCTGTCTATCTGTACCTAAA
TGGTTGCTCACTATGCATTTTCTGTGCTCTTCGCCCTTTTTATTTAATGTATG
GATATTTATGCTGCTTCCAGAATGGATCTAAAGCTCTTTGTTTCTAGGTTTTC
TCCCCCATCCTTCTAGGCATCTCTCACACTGTCTAGGCCAGACACCATGTCT
GCTGCCTGAATCTGTAGACACCATTTATAAAGCACGTACTCACCGAGTTTGT
ATTTGGCTTGTTCTGTGTCTGATTAAAGGGAGACCATGAGTCCCCAGGGTA
CACTGAGTTACCCCAGTACCAAGGGGGAGCCTTGTTTGTGTCTCCATGGCA
GAAGCAGGCCTGGAGCCATTTTGGTTTCTTCCTTGACTTCTCTCAAACACAG
ACGCCTCACTTGCTCATTACAGGTTCTCCTTTGGGAATGTCAGCATTGCTCC
TTGACTGCTGGCTGCCCTGGAAGGAGCCCATTAGCTCTGTGTGAGCCCTTG
ACAGCTACTGCCTCTCCTTACCACAGGGGCCTCTAAGATACTGTTACCTAGA
GGTCTTGAGGATCTGTGTTCTCTGGGGGGAGGAAAGGAGGAGGAACCCAG
AACTTTCTTACAGTTTTCCTTGTTCTGTCACATGTCAAGACTGAAGGAACAG
GCTGGGCTACGTAGTGAGATCCTGTCTCAAAGGAAAGACGAGCATAGCCGA
ACCCCGGTGGAACCCCCTCTGTTACCTGTTCACACAAGCTTATTGATGAGT
CTCATGTTAATGTCTTGTTTGTATGAAGTTTAAGAAAATATCGGGTTGGGCAA
CACATTCTATTTATTCATTTTATTTGAAATCTTAATGCCATCTCATGGTGTTGG
ATTGGTGTGGCACTTTATTCTTTTGTGTTGTGTATAACCATAAATTTTATTTTG
CATCAGATTGTCAATGTATTGCATTAATTTAATAAATATTTTTATTTATTAAAAA
AAAAAAAAAAAAAAAA
```

FIG. 6

MRIFAGIIFTACCHLLRAFTITAPKDLYVVEYGSNVTMECRFPVERELDLLALVVWEKEDEQVIQFVAGEE
DLKPQHSNFRGRASLPKDQLLKGNAALQITDVKLQDAGVYCCIISYGGADYKRITLKVNAPYRKINQRISV
DPATSEHELICQAEGYPEAEVIWTNSDHQPVSGKRSVTTSRTEGMLLNVTSSLRVNATANDVFYCTFWR
SQPGQNHTAELIIPELPATHPPQNRTHWVLLGSILLFLIVVSTVLLFLRKQVRMLDVEKCGVEDTSSKNRN
DTQFEET.

FIG. 7 mB7-4 vs. hB7-4

69% identity

```
mB7-4   1   MRIFAGIIFTACCHLLRAFTITAPKDLYVVEYGSNVTMECRFPVERELDLLALVVYWEKE   60
            MRIFA  IF    HLL AFT+T PKDLYVVEYGSN+T+EC+FPVE++LDL AL+VYWE E
hB7-4   1   MRIFAVFIFMTYWHLLNAFTVTVPKDLYVVEYGSNMTIECKFPVEKQLDLAALIVYWEME   60 mB7-4   61  DEQVIQFVAGEEDLKPQHSNFRGRASLPKDQLLKGNAALQITDVKLQDAGVYCCIISYGG   120
            D+ +IQFV GEEDLK QHS++R RA L KDQL GNAALQITDVKLQDAGVY C+ISYGG
hB7-4   61  DKNIIQFVHGEEDLKVQHSSYRQRARLLKDQLSLGNAALQITDVKLQDAGVYRCMISYGG   120 mB7-4   121 ADYKRITLKVNAPYRKINQRI-SVDPATSEHELICQAEGYPEAEVIWTNSDHQPVSGKRS   179
            ADYKRIT+KVNAPY KINQRI    VDP TSEHEL CQAEGYP +AEVIWT+SDHQ +SGK +
hB7-4   121 ADYKRITVKVNAPYNKINQRILVVDPVTSEHELTCQAEGYPKAEVIWTSSDHQVLSGKTT   180 mB7-4   180 VTTSRTEGMLINVTSSLRVNATANDVFYCTFWRSQPGQNHTAELIIPELPATHPPQNRTH   239
            T S+ E  L NVTS+LR+N T N++FYCTF R  P +NHTAEL+IPELP HPP RTH
hB7-4   181 TTNSKREEKLFNVTSTLRINTTTNEIFYCTFRRLDPEENHTAELVIPELPLAHPPNERTH   240 mB7-4   240 WVLLGSILLFLIVVSTVLLFLRKQVRMLDVEKCGVEDTSSKNRNDTQFEET           290
            V+LG+ILL L V   T +  LRK  RM+DV+KCG++DT+SK  ++DT  EET
hB7-4   241 LVILGAILLCLGVALTFIFRLRKG-RMMDVKKCGIQDTNSKKQSDTHLEET           290
```

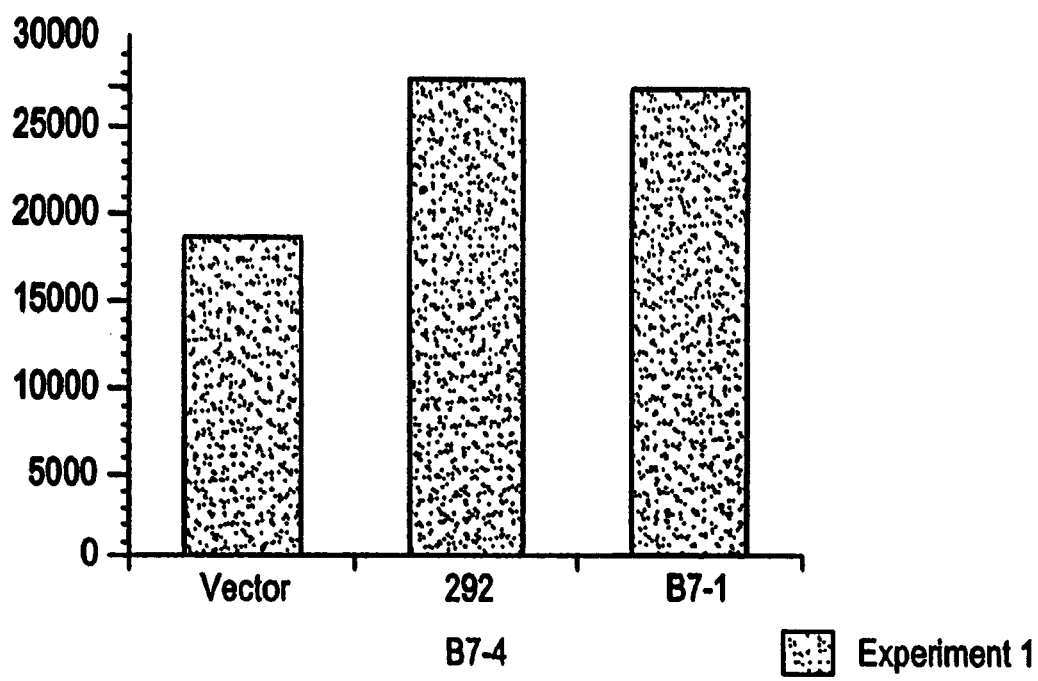
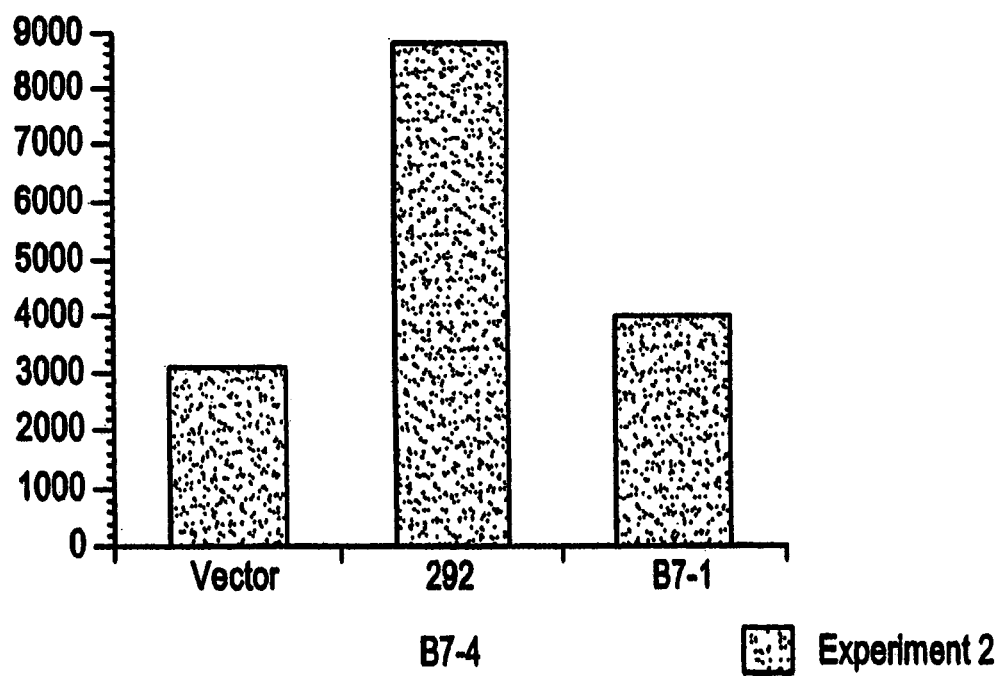

SEQUENCE LISTING

```
<160> NUMBER OF SEQ ID NOS: 11

<210> SEQ ID NO 1
<211> LENGTH: 968
<212> TYPE: DNA
<213> ORGANISM: Homo sapiens
<220> FEATURE:
<221> NAME/KEY: CDS
<222> LOCATION: (59)..(793)
```

```
<400> SEQUENCE: 1
gcttcccgag gctccgcacc agccgcgctt ctgtccgcct gcagggcatt ccagaaag            58 atg agg ata ttt gct gtc ttt ata ttc atg acc tac tgg cat ttg ctg           106
Met Arg Ile Phe Ala Val Phe Ile Phe Met Thr Tyr Trp His Leu Leu
  1               5                  10                  15 aac gca ttt act gtc acg gtt ccc aag gac cta tat gtg gta gag tat           154
Asn Ala Phe Thr Val Thr Val Pro Lys Asp Leu Tyr Val Val Glu Tyr
             20                  25                  30 ggt agc aat atg aca att gaa tgc aaa ttc cca gta gaa aaa caa tta           202
Gly Ser Asn Met Thr Ile Glu Cys Lys Phe Pro Val Glu Lys Gln Leu
         35                  40                  45 gac ctg gct gca cta att gtc tat tgg gaa atg gag gat aag aac att           250
Asp Leu Ala Ala Leu Ile Val Tyr Trp Glu Met Glu Asp Lys Asn Ile
     50                  55                  60 att caa ttt gtg cat gga gag gaa gac ctg aag gtt cag cat agt agc           298
Ile Gln Phe Val His Gly Glu Glu Asp Leu Lys Val Gln His Ser Ser
 65                  70                  75                  80 tac aga cag agg gcc cgg ctg ttg aag gac cag ctc tcc ctg gga aat           346
Tyr Arg Gln Arg Ala Arg Leu Leu Lys Asp Gln Leu Ser Leu Gly Asn
                 85                  90                  95 gct gca ctt cag atc aca gat gtg aaa ttg cag gat gca ggg gtg tac           394
Ala Ala Leu Gln Ile Thr Asp Val Lys Leu Gln Asp Ala Gly Val Tyr
            100                 105                 110 cgc tgc atg atc agc tat ggt ggt gcc gac tac aag cga att act gtg           442
Arg Cys Met Ile Ser Tyr Gly Gly Ala Asp Tyr Lys Arg Ile Thr Val
        115                 120                 125 aaa gtc aat gcc cca tac aac aaa atc aac caa aga att ttg gtt gtg           490
Lys Val Asn Ala Pro Tyr Asn Lys Ile Asn Gln Arg Ile Leu Val Val
    130                 135                 140 gat cca gtc acc tct gaa cat gaa ctg aca tgt cag gct gag ggc tac           538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt           586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat           634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac           682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg           730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca           778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt          833
Leu Ser Pro Ser Thr
                245 gaataaatga atgaatgaat aacactatgt ttacaaaata tatcctaatt cctcacctcc          893 attcatccaa accatattgt tacttaataa acattcagca gatatttatg gaataaaaaa          953 aaaaaaaaaa aaaaa                                                          968

<210> SEQ ID NO 2
<211> LENGTH: 245
<212> TYPE: PRT
```

<213> ORGANISM: Homo sapiens

<400> SEQUENCE: 2

```
Met Arg Ile Phe Ala Val Phe Ile Phe Met Thr Tyr Trp His Leu Leu
 1               5                   10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
     50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245
```

<210> SEQ ID NO 3
<211> LENGTH: 1553
<212> TYPE: DNA
<213> ORGANISM: Homo sapiens
<220> FEATURE:
<221> NAME/KEY: CDS
<222> LOCATION: (53)..(922)

<400> SEQUENCE: 3

```
cgaggctccg caccagccgc gcttctgtcc gcctgcaggg cattccagaa ag atg agg         58
                                                          Met Arg
                                                           1 ata ttt gct gtc ttt ata ttc atg acc tac tgg cat ttg ctg aac gca         106
Ile Phe Ala Val Phe Ile Phe Met Thr Tyr Trp His Leu Leu Asn Ala
        5                   10                  15 ttt act gtc acg gtt ccc aag gac cta tat gtg gta gag tat ggt agc         154
Phe Thr Val Thr Val Pro Lys Asp Leu Tyr Val Val Glu Tyr Gly Ser
 20                  25                  30 aat atg aca att gaa tgc aaa ttc cca gta gaa aaa caa tta gac ctg         202
Asn Met Thr Ile Glu Cys Lys Phe Pro Val Glu Lys Gln Leu Asp Leu
         35                  40                  45                  50
```

-continued

| | |
|---|---|
| gct gca cta att gtc tat tgg gaa atg gag gat aag aac att att caa<br>Ala Ala Leu Ile Val Tyr Trp Glu Met Glu Asp Lys Asn Ile Ile Gln<br>             55                     60                     65 | 250 |
| ttt gtg cat gga gag gaa gac ctg aag gtt cag cat agt agc tac aga<br>Phe Val His Gly Glu Glu Asp Leu Lys Val Gln His Ser Ser Tyr Arg<br>             70                     75                     80 | 298 |
| cag agg gcc cgg ctg ttg aag gac cag ctc tcc ctg gga aat gct gca<br>Gln Arg Ala Arg Leu Leu Lys Asp Gln Leu Ser Leu Gly Asn Ala Ala<br>         85                     90                     95 | 346 |
| ctt cag atc aca gat gtg aaa ttg cag gat gca ggg gtg tac cgc tgc<br>Leu Gln Ile Thr Asp Val Lys Leu Gln Asp Ala Gly Val Tyr Arg Cys<br>100                      105                   110 | 394 |
| atg atc agc tat ggt ggt gcc gac tac aag cga att act gtg aaa gtc<br>Met Ile Ser Tyr Gly Gly Ala Asp Tyr Lys Arg Ile Thr Val Lys Val<br>115                      120                   125                   130 | 442 |
| aat gcc cca tac aac aaa atc aac caa aga att ttg gtt gtg gat cca<br>Asn Ala Pro Tyr Asn Lys Ile Asn Gln Arg Ile Leu Val Val Asp Pro<br>             135                   140                   145 | 490 |
| gtc acc tct gaa cat gaa ctg aca tgt cag gct gag ggc tac ccc aag<br>Val Thr Ser Glu His Glu Leu Thr Cys Gln Ala Glu Gly Tyr Pro Lys<br>             150                   155                   160 | 538 |
| gcc gaa gtc atc tgg aca agc agt gac cat caa gtc ctg agt ggt aag<br>Ala Glu Val Ile Trp Thr Ser Ser Asp His Gln Val Leu Ser Gly Lys<br>             165                   170                   175 | 586 |
| acc acc acc acc aat tcc aag aga gag gag aag ctt ttc aat gtg acc<br>Thr Thr Thr Thr Asn Ser Lys Arg Glu Glu Lys Leu Phe Asn Val Thr<br>180                      185                   190 | 634 |
| agc aca ctg aga atc aac aca aca act aat gag att ttc tac tgc act<br>Ser Thr Leu Arg Ile Asn Thr Thr Thr Asn Glu Ile Phe Tyr Cys Thr<br>195                      200                   205                   210 | 682 |
| ttt agg aga tta gat cct gag gaa aac cat aca gct gaa ttg gtc atc<br>Phe Arg Arg Leu Asp Pro Glu Glu Asn His Thr Ala Glu Leu Val Ile<br>             215                   220                   225 | 730 |
| cca gaa cta cct ctg gca cat cct cca aat gaa agg act cac ttg gta<br>Pro Glu Leu Pro Leu Ala His Pro Pro Asn Glu Arg Thr His Leu Val<br>             230                   235                   240 | 778 |
| att ctg gga gcc atc tta tta tgc ctt ggt gta gca ctg aca ttc atc<br>Ile Leu Gly Ala Ile Leu Leu Cys Leu Gly Val Ala Leu Thr Phe Ile<br>         245                     250                   255 | 826 |
| ttc cgt tta aga aaa ggg aga atg atg gat gtg aaa aaa tgt ggc atc<br>Phe Arg Leu Arg Lys Gly Arg Met Met Asp Val Lys Lys Cys Gly Ile<br>         260                     265                   270 | 874 |
| caa gat aca aac tca aag aag caa agt gat aca cat ttg gag gag acg<br>Gln Asp Thr Asn Ser Lys Lys Gln Ser Asp Thr His Leu Glu Glu Thr<br>275                      280                   285                   290 | 922 |
| taatccagca ttggaacttc tgatcttcaa gcagggattc tcaacctgtg ttttaggggt | 982 |
| tcatcgggc tgagcgtgac aagaggaagg aatgggcccg tgggatgcag caatgtggg | 1042 |
| acttaaaagg cccaagcact gaaaatggaa cctggcgaaa gcagaggagg agaatgaaga | 1102 |
| aagatggagt caaacaggga gcctggaggg agaccttgat actttcaaat gcctgagggg | 1162 |
| ctcatcgacg cctgtgacag ggagaaagga tacttctgaa caaggagcct ccaagcaaat | 1222 |
| catccattgc tcatcctagg aagacgggtt gagaatccct aatttgaggg tcagttcctg | 1282 |
| cagaagtgcc ctttgcctcc actcaatgcc tcaatttgtt ttctgcatga ctgagagtct | 1342 |
| cagtgttgga acgggacagt atttatgtat gagttttttcc tatttatttt gagtctgtga | 1402 |
| ggtcttcttg tcatgtgagt gtggttgtga atgatttctt ttgaagatat attgtagtag | 1462 |
| atgttacaat tttgtcgcca aactaaactt gctgcttaat gatttgctca catctagtaa | 1522 |

```
aacatggagt atttgtaaaa aaaaaaaaaa a                                    1553
```

<210> SEQ ID NO 4
<211> LENGTH: 290
<212> TYPE: PRT
<213> ORGANISM: Homo sapiens

<400> SEQUENCE: 4

```
Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
         50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 5
<211> LENGTH: 24
<212> TYPE: DNA
<213> ORGANISM: Homo sapiens

<400> SEQUENCE: 5

```
cagctatggt ggtgccgact acaa                                             24
```

<210> SEQ ID NO 6
<211> LENGTH: 25
<212> TYPE: DNA
<213> ORGANISM: Homo sapiens

<400> SEQUENCE: 6
aggtgctagg ggacagtgtt agaca                                    25

<210> SEQ ID NO 7
<211> LENGTH:
<212> TYPE:
<213> ORGANISM:

<400> SEQUENCE: 7

000

<210> SEQ ID NO 8
<211> LENGTH:
<212> TYPE:
<213> ORGANISM:

<400> SEQUENCE: 8

000

<210> SEQ ID NO 9
<211> LENGTH: 24
<212> TYPE: DNA
<213> ORGANISM: Homo sapiens

<400> SEQUENCE: 9
tcgcttgtag tcggcaccac cata                                     24

<210> SEQ ID NO 10
<211> LENGTH: 3593
<212> TYPE: DNA
<213> ORGANISM: Mus musculus
<220> FEATURE:
<221> NAME/KEY: CDS
<222> LOCATION: (17)..(889)

<400> SEQUENCE: 10

```
agatagttcc caaaac atg agg ata ttt gct ggc att ata ttc aca gcc tgc      52
               Met Arg Ile Phe Ala Gly Ile Ile Phe Thr Ala Cys
                 1               5                  10 tgt cac ttg cta cgg gcg ttt act atc acg gct cca aag gac ttg tac        100
Cys His Leu Leu Arg Ala Phe Thr Ile Thr Ala Pro Lys Asp Leu Tyr
            15                  20                  25 gtg gtg gag tat ggc agc aac gtc acg atg gag tgc aga ttc cct gta        148
Val Val Glu Tyr Gly Ser Asn Val Thr Met Glu Cys Arg Phe Pro Val
         30                  35                  40 gaa cgg gag ctg gac ctg ctt gcg tta gtg gtg tac tgg gaa aag gaa        196
Glu Arg Glu Leu Asp Leu Leu Ala Leu Val Val Tyr Trp Glu Lys Glu
 45                  50                  55                  60 gat gag caa gtg att cag ttt gtg gca gga gag gag gac ctt aag cct        244
Asp Glu Gln Val Ile Gln Phe Val Ala Gly Glu Glu Asp Leu Lys Pro
                 65                  70                  75 cag cac agc aac ttc agg ggg aga gcc tcg ctg cca aag gac cag ctt        292
Gln His Ser Asn Phe Arg Gly Arg Ala Ser Leu Pro Lys Asp Gln Leu
             80                  85                  90 ttg aag gga aat gct gcc ctt cag atc aca gac gtc aag ctg cag gac        340
Leu Lys Gly Asn Ala Ala Leu Gln Ile Thr Asp Val Lys Leu Gln Asp
         95                  100                 105 gca ggc gtt tac tgc tgc ata atc agc tac ggt ggt gcg gac tac aag        388
```

-continued

```
          Ala Gly Val Tyr Cys Cys Ile Ile Ser Tyr Gly Gly Ala Asp Tyr Lys
              110                 115                 120 cga atc acg ctg aaa gtc aat gcc cca tac cgc aaa atc aac cag aga        436
Arg Ile Thr Leu Lys Val Asn Ala Pro Tyr Arg Lys Ile Asn Gln Arg
125                 130                 135                 140 att tcc gtg gat cca gcc act tct gag cat gaa cta ata tgt cag gcc        484
Ile Ser Val Asp Pro Ala Thr Ser Glu His Glu Leu Ile Cys Gln Ala
                145                 150                 155 gag ggt tat cca gaa gct gag gta atc tgg aca aac agt gac cac caa        532
Glu Gly Tyr Pro Glu Ala Glu Val Ile Trp Thr Asn Ser Asp His Gln
                160                 165                 170 ccc gtg agt ggg aag aga agt gtc acc act tcc cgg aca gag ggg atg        580
Pro Val Ser Gly Lys Arg Ser Val Thr Thr Ser Arg Thr Glu Gly Met
            175                 180                 185 ctt ctc aat gtg acc agc agt ctg agg gtc aac gcc aca gcg aat gat        628
Leu Leu Asn Val Thr Ser Ser Leu Arg Val Asn Ala Thr Ala Asn Asp
        190                 195                 200 gtt ttc tac tgt acg ttt tgg aga tca cag cca ggg caa aac cac aca        676
Val Phe Tyr Cys Thr Phe Trp Arg Ser Gln Pro Gly Gln Asn His Thr
205                 210                 215                 220 gcg gag ctg atc atc cca gaa ctg cct gca aca cat cct cca cag aac        724
Ala Glu Leu Ile Ile Pro Glu Leu Pro Ala Thr His Pro Pro Gln Asn
                225                 230                 235 agg act cac tgg gtg ctt ctg gga tcc atc ctg ttc ctc att gta             772
Arg Thr His Trp Val Leu Leu Gly Ser Ile Leu Phe Leu Ile Val
                240                 245                 250 gtg tcc acg gtc ctc ctc ttc ttg aga aaa caa gtg aga atg cta gat        820
Val Ser Thr Val Leu Leu Phe Leu Arg Lys Gln Val Arg Met Leu Asp
            255                 260                 265 gtg gag aaa tgt ggc gtt gaa gat aca agc tca aaa aac cga aat gat        868
Val Glu Lys Cys Gly Val Glu Asp Thr Ser Ser Lys Asn Arg Asn Asp
        270                 275                 280 aca caa ttc gag gag acg taa gcagtgttga accctctgat cgtcgattgg           919
Thr Gln Phe Glu Glu Thr
285                 290 cagcttgtgg tctgtgaaag aaagggccca tgggacatga gtccaaagac tcaagatgga      979
acctgaggga gagaaccaag aaagtgttgg gagaggagcc tggaacaacg dacatttttt     1039
ccagggagac actgctaagc aagttgccca tcagtcgtct tgggaaatgg attgagggtt     1099
cctggcttag cagctggtcc ttgcacagtg acctttcct ctgctcagtg ccgggatgag      1159
agatggagtc atgagtgttg aagaataagt gccttctatt tattttgagt ctgtgtgttc     1219
tcactttggg catgtaatta tgactggtga attctgacga catgatagat cttaagatgt     1279
agtcaccaaa ctcaactgct gcttagcatc ctccgtaact actgatacaa gcagggaaca     1339
cagaggtcac ctgcttggtt tgacaggctc ttgctgtctg actcaaataa tctttatttt     1399
tcagtcctca aggctcttcg atagcagttg ttctgtatca gccttatagg tgtcaggtat     1459
agcactcaac atctcatctc attacaatag caaccctcat caccatagca acagctaacc     1519
tctgttatcc tcacttcata gccaggaagc tgagcgacta agtcacttgc ccacagagta     1579
tcagctctca gatttctgtt cttcagccac tgtcctttca ggatagaatt tgtcgttaag     1639
aaattaattt aaaaactgat tattgagtag cattgtatat caatcacaac atgccttgtg     1699
cactgtgctg gcctctgagc ataaagatgt acgccggagt accggtcgga catgtttatg     1759
tgtgttaaat actcagagaa atgttcatta caaggagct tgcattttag agacactgga      1819
aagtaactcc agttcattgt ctagcattac atttacctca tttgctatcc ttgccataca     1879
```

-continued

```
gtctcttgtt ctccatgaag tgtcatgaat cttgttgaat agttcttta ttttttaaat   1939
gtttctattt aaatgatatt gacatctgag gcgatagctc agttggtaaa acccttcct    1999
cacaagtgtg aaaccctgag tcttatccct agaacccaca taaaaaacag ttgcgtatgt   2059
ttgtgcatgc ttttgatccc agcactaggg aggcagaggc aggcagatcc tgagctctca   2119
ttgaccaccc agcctagcct acatggttag ctccaggcct acaggagctg gcagagcctg   2179
aaaaacgatg cctagacaca cacacacaca cacacacaca cacacacaca cacacacacc   2239
atgtactcat agacctaagt gcaccctcct acacatgcac acacataccaa ttcaaacaca   2299
aatcaacagg gaattgtctc agaatggtcc ccaagacaaa gaagaagaaa aacaccaaac   2359
cagctctatt ccctcagcct atcctctcta ctccttccta gaagcaacta ctattgtttt   2419
tgtatataaa tttacccaac gacagttaat atgtagaata tatattaaag tgtctgtcaa   2479
tatatattat ctctttcttt cttcttcct ttctttcttt ctttctttct ttctttcttt   2539
ctttctttct ttctttcttt cttccttcct tccttccttc cttccttcct tccttccttt   2599
ctttctttct ttctttttt ctgtctatct gtacctaaat ggttgctcac tatgcatttt   2659
ctgtgctctt cgccctttt atttaatgta tggatattta tgctgcttcc agaatggatc   2719
taaagctctt tgtttctagg ttttctcccc catccttcta ggcatctctc acactgtcta   2779
ggccagacac catgtctgct gcctgaatct gtagacacca tttataaagc acgtactcac   2839
cgagtttgta tttggcttgt tctgtgtctg attaaaggga gaccatgagt ccccagggta   2899
cactgagtta ccccagtacc aagggggagc cttgtttgtg tctccatggc agaagcaggc   2959
ctggagccat tttggtttct tccttgactt ctctcaaaca cagacgcctc acttgctcat   3019
tacaggttct ccttttgggaa tgtcagcatt gctccttgac tgctggctgc cctggaagga   3079
gcccattagc tctgtgtgag cccttgacag ctactgcctc tccttaccac aggggcctct   3139
aagatactgt tacctagagg tcttgaggat ctgtgttctc tgggggggagg aaaggaggag   3199
gaacccagaa ctttcttaca gttttccttg ttctgtcaca tgtcaagact gaaggaacag   3259
gctgggctac gtagtgagat cctgtctcaa aggaaagacg agcatagccg aaccccccggt   3319
ggaacccct ctgttacctg ttcacacaag cttattgatg agtctcatgt taatgtcttg   3379
tttgtatgaa gtttaagaaa atatcgggtt gggcaacaca ttctatttat tcatttatt    3439
tgaaatctta atgccatctc atggtgttgg attggtgtgg cactttattc ttttgtgttg   3499
tgtataacca taaatttttat tttgcatcag attgtcaatg tattgcatta atttaataaa   3559
tattttatt tattaaaaaa aaaaaaaaaa aaaa                                3593
```

<210> SEQ ID NO 11
<211> LENGTH: 290
<212> TYPE: PRT
<213> ORGANISM: Mus musculus

<400> SEQUENCE: 11

```
Met Arg Ile Phe Ala Gly Ile Ile Phe Thr Ala Cys Cys His Leu Leu
  1               5                  10                  15

Arg Ala Phe Thr Ile Thr Ala Pro Lys Asp Leu Tyr Val Val Glu Tyr
             20                  25                  30

Gly Ser Asn Val Thr Met Glu Cys Arg Phe Pro Val Glu Arg Glu Leu
         35                  40                  45

Asp Leu Leu Ala Leu Val Val Tyr Trp Glu Lys Glu Asp Glu Gln Val
     50                  55                  60

Ile Gln Phe Val Ala Gly Glu Glu Asp Leu Lys Pro Gln His Ser Asn
```

-continued

```
            65                  70                  75                  80
        Phe Arg Gly Arg Ala Ser Leu Pro Lys Asp Gln Leu Leu Lys Gly Asn
                        85                  90                  95

Ala Ala Leu Gln Ile Thr Asp Val Lys Leu Gln Asp Ala Gly Val Tyr
                       100                 105                 110

Cys Cys Ile Ile Ser Tyr Gly Gly Ala Asp Tyr Lys Arg Ile Thr Leu
                       115                 120                 125

Lys Val Asn Ala Pro Tyr Arg Lys Ile Asn Gln Arg Ile Ser Val Asp
                       130                 135                 140

Pro Ala Thr Ser Glu His Glu Leu Ile Cys Gln Ala Glu Gly Tyr Pro
        145                 150                 155                 160

Glu Ala Glu Val Ile Trp Thr Asn Ser Asp His Gln Pro Val Ser Gly
                       165                 170                 175

Lys Arg Ser Val Thr Thr Ser Arg Thr Glu Gly Met Leu Leu Asn Val
                       180                 185                 190

Thr Ser Ser Leu Arg Val Asn Ala Thr Ala Asn Asp Val Phe Tyr Cys
                       195                 200                 205

Thr Phe Trp Arg Ser Gln Pro Gly Gln Asn His Thr Ala Glu Leu Ile
                       210                 215                 220

Ile Pro Glu Leu Pro Ala Thr His Pro Pro Gln Asn Arg Thr His Trp
        225                 230                 235                 240

Val Leu Leu Gly Ser Ile Leu Leu Phe Leu Ile Val Val Ser Thr Val
                       245                 250                 255

Leu Leu Phe Leu Arg Lys Gln Val Arg Met Leu Asp Val Glu Lys Cys
                       260                 265                 270

Gly Val Glu Asp Thr Ser Ser Lys Asn Arg Asn Asp Thr Gln Phe Glu
                       275                 280                 285

Glu Thr
        290
```

US 7,038,013 B2

B7-4 POLYPEPTIDES AND USES THEREFOR

RELATED APPLICATIONS

This application is a divisional application of U.S. application Ser. No. 09/644,934, filed Aug. 23, 2000, Now U.S. Pat. No. 6,936,704 pending. This application claims priority to U.S. provisional application Ser. No. 60/150,390, filed on Aug. 23, 1999, which is incorporated herein in its entirety by this reference.

GOVERNMENT FUNDING

Work described herein was supported under AI 39671, AI 44690, CA 94500 and AI 41584 awarded by the National Institutes of Health. The U.S. government therefore may have certain rights in this invention.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165, 302–319; Mueller, D. L., et al. (1990) *J. Immunol.* 144, 3701–3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. 1996. *Annu. Rev. Immunol.* 14:233). Costimulation is neither antigen-specific, nor MHC restricted and is thought to be provided by one or more distinct cell surface molecules expressed by APCs (Jenkins, M. K., et al. 1988 *J. Immunol.* 140, 3324–3330; Linsley, P. S., et al. 1991 *J. Exp. Med.* 173, 721–730; Gimmi, C. D., et al., 1991 *Proc. Natl. Acad. Sci. USA.* 88, 6575–6579; Young, J. W., et al. 1992 *J. Clin. Invest.* 90, 229–237; Koulova, L., et al. 1991 *J. Exp. Med.* 173, 759–762; Reiser, H., et al. 1992 *Proc. Natl. Acad. Sci. USA.* 89, 271–275; van-Seventer, G. A., et al. (1990) *J. Immunol.* 144, 4579–4586; LaSalle, J. M., et al., 1991 *J. Immunol.* 147, 774–80; Dustin, M. I., et al., 1989 *J. Exp. Med.* 169, 503; Armitage, R. J., et al. 1992 *Nature* 357, 80–82; Liu, Y., et al. 1992 *J. Exp. Med.* 175, 437–445).

The CD80 (B7-1) and CD86 (B7-2) proteins, expressed on APCs, are critical costimulatory molecules (Freeman et al. 1991. *J. Exp. Med.* 174:625; Freeman et al. 1989 *J. Immunol.* 143:2714; Azuma et al. 1993 *Nature* 366:76; Freeman et al. 1993. *Science* 262:909). B7-2 appears to play a predominant role during primary immune responses, while B7-1, which is upregulated later in the course of an immune response, may be important in prolonging primary T cell responses or costimulating secondary T cell responses (Bluestone. 1995. *Immunity.* 2:555).

One ligand to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S., et al. 1991 *J. Exp. Med.* 173, 721–730; Gimmi, C. D., et al. 1991 *Proc. Natl. Acad. Sci. USA.* 88, 6575–6579; June, C. H., et al. 1990 *Immunol. Today.* 11, 211–6; Harding, F. A., et al. 1992 *Nature.* 356, 607–609). A second ligand, termed CTLA4 (CD152) is homologous to CD28 but is not expressed on resting T cells and appears following T cell activation (Brunet, J. F., et al., 1987 *Nature* 328, 267–270). CTLA4 appears to be critical in negative regulation of T cell responses (Waterhouse et al. 1995. *Science* 270:985). Blockade of CTLA4 has been found to remove inhibitory signals, while aggregation of CTLA4 has been found to provide inhibitory signals that downregulate T cell responses (Allison and Krummel. 1995. *Science* 270:932). The B7 molecules have a higher affinity for CTLA4 than for CD28 (Linsley, P. S., et al., 1991 *J. Exp. Med.* 174, 561–569) and B7-1 and B7-2 have been found to bind to distinct regions of the CTLA4 molecule and have different kinetics of binding to CTLA4 (Linsley et al. 1994. *Immunity.* 1:793). A new molecule related to CD28 and CTLA4, ICOS, has been identified (Hutloff et al. 1999. *Nature.* 397:263; WO 98/38216), as has its ligand, which is a new B7 family member (Aicher A. et al. (2000) *J. Immunol.* 164:4689–96; Mages H. W. et al. (2000) *Eur. J. Immunol.* 30:1040–7; Brodie D. et al. (2000) *Curr. Biol.* 10:333–6; Ling V. et al. (2000) *J. Immunol.* 164:1653–7; Yoshinaga S. K. et al. (1999) *Nature* 402:827–32). If T cells are only stimulated through the T cell receptor, without receiving an additional costimulatory signal, they become nonresponsive, anergic, or die, resulting in downmodulation of the immune response.

The importance of the B7:CD28/CTLA4 costimulatory pathway has been demonstrated in vitro and in several in vivo model systems. Blockade of this costimulatory pathway results in the development of antigen specific tolerance in murine and humans systems (Harding, F. A., et al. (1992) *Nature.* 356, 607–609; Lenschow, D. J., et al. (1992) *Science.* 257, 789–792; Turka, L. A., et al. (1992) *Proc. Natl. Acad. Sci. USA.* 89, 11102–11105; Gimmi, C. D., et al. (1993) *Proc. Natl. Acad. Sci USA* 90, 6586–6590; Boussiotis, V., et al. (1993) *J. Exp. Med.* 178, 1753–1763). Conversely, expression of B7 by B7 negative murine tumor cells induces T-cell mediated specific immunity accompanied by tumor rejection and long lasting protection to tumor challenge (Chen, L., et al. (1992) *Cell* 71, 1093–1102; Townsend, S. E. and Allison, J. P. (1993) *Science* 259, 368–370; Baskar, S., et al. (1993) *Proc. Natl. Acad. Sci.* 90, 5687–5690.). Therefore, manipulation of the costimulatory pathways offers great potential to stimulate or suppress immune responses in humans.

SUMMARY OF THE INVENTION

The present invention is based, at least in part, on the discovery of novel nucleic acid molecules and polypeptides encoded by such nucleic acid molecules, referred to herein as the B7-4 family. Preferred B7-4 molecules include antigens on the surface of professional antigen presenting cells (e.g., B lymphocytes, monocytes, dendritic cells, Langerhan cells) and other antigen presenting cells (e.g., keratinocytes, endothelial cells, astrocytes, fibroblasts, oligodendrocytes), costimulate T cell proliferation and/or are bound by antibodies which recognize B7 members, e.g., anti-BB1 antibodies. The B7-4 nucleic acid and polypeptide molecules of the present invention are useful, e.g., in modulating the immune response. Accordingly, in one aspect, this invention provides isolated nucleic acid molecules encoding B7-4 polypeptides, as well as nucleic acid fragments suitable as primers or hybridization probes for the detection of B7-4-encoding nucleic acids.

In one embodiment, a B7-4 nucleic acid molecule of the invention is at least 50%, 55%, 60%, 65%, 70%, 75%, 80%, 85%, 90%, 95%, 98% or more identical to a nucleotide sequence (e.g., to the entire length of the nucleotide sequence) including SEQ ID NO:1 or 3, or a complement thereof.

In a preferred embodiment, the isolated nucleic acid molecule includes the nucleotide sequence shown SEQ ID NO:1 or 3, or a complement thereof. In another preferred embodiment, an isolated nucleic acid molecule of the invention encodes the amino acid sequence of a B7-4 polypeptide.

Another embodiment of the invention features nucleic acid molecules, preferably the B7-4 nucleic acid molecules, which specifically detect the B7-4 nucleic acid molecules relative to nucleic acid molecules encoding non- the B7-4 polypeptides. For example, in one embodiment, such a nucleic acid molecule is at least 20, 30, 40, 50, 100, 150, 200, 250, 300, 350, 400, 450, 500, 550, 600, 650, 700, 750, or 800 nucleotides in length and hybridizes under stringent conditions to a nucleic acid molecule comprising the nucleotide sequence shown in SEQ ID NO:1 or 3, or a complement thereof.

In other preferred embodiments, the nucleic acid molecule encodes a naturally occurring allelic variant of a human B7-4 polypeptide, wherein the nucleic acid molecule hybridizes to a nucleic acid molecule which includes SEQ ID NO:1 or 3 under stringent conditions.

Another embodiment of the invention provides an isolated nucleic acid molecule which is antisense to a B7-4 nucleic acid molecule, e.g., the coding strand of a B7-4 nucleic acid molecule.

Another aspect of the invention provides a vector comprising a B7-4 nucleic acid molecule. In certain embodiments, the vector is a recombinant expression vector. In another embodiment, the invention provides a host cell containing a vector of the invention. The invention also provides a method for producing a polypeptide, preferably a B7-4 polypeptide, by culturing in a suitable medium, a host cell, e.g., a mammalian host cell such as a non-human mammalian cell, of the invention containing a recombinant expression vector, such that the polypeptide is produced.

Another aspect of this invention features isolated or recombinant B7-4 polypeptides and proteins. In one embodiment, the isolated polypeptide, is a human or murine B7-4 polypeptide. In yet another embodiment, the isolated B7-4 polypeptide is a soluble B7-4 polypeptide. In a further embodiment, the isolated B7-4 polypeptide, is expressed on the surface of a cell, e.g., has a transmembrane domain.

In a further embodiment, the isolated B7-4 polypeptide plays a role in costimulating the cytokine secretion and/or proliferation of activated T cells. In another embodiment, the isolated B7-4 polypeptide is encoded by a nucleic acid molecule having a nucleotide sequence which hybridizes under stringent hybridization conditions to a nucleic acid molecule comprising the nucleotide sequence of SEQ ID NO:1 or 3.

Another embodiment of the invention features an isolated polypeptide, preferably a B7-4 polypeptide, which is encoded by a nucleic acid molecule having a nucleotide sequence at least about 50%, 55%, 60%, 65%, 70%, 75%, 80%, 85%, 90%, 95%, 98% or more identity to a nucleotide sequence (e.g., to the entire length of the nucleotide sequence) including SEQ ID NO:1 or 3 or a complement thereof.

Another embodiment of the invention features an isolated polypeptide, preferably a B7-4 polypeptide, which is encoded by a nucleic acid molecule having a nucleotide sequence at least about 50%, 55%, 60%, 65%, 70%, 75%, 80%, 85%, 90%, 95%, 98% or more identity to an amino acid sequence (e.g., to the entire length of the amino acid sequence) including SEQ ID NO:2 or 4.

This invention further features an isolated B7-4 polypeptide which is encoded by a nucleic acid molecule having a nucleotide sequence which hybridizes under stringent hybridization conditions to a nucleic acid molecule comprising the nucleotide sequence of SEQ ID NO:1 or 3, or a complement thereof.

The polypeptides of the present invention can be operatively linked to a non-B7-4 polypeptide (e.g., heterologous amino acid sequences) to form fusion proteins. The invention further features antibodies, such as monoclonal or polyclonal antibodies, that specifically bind polypeptides of the invention, preferably B7-4 polypeptides. In addition, the B7-4 polypeptides, e.g., biologically active polypeptides, can be incorporated into pharmaceutical compositions, which optionally include pharmaceutically acceptable carriers.

In another aspect, the present invention provides a method for detecting the presence of a B7-4 nucleic acid molecule or polypeptide in a biological sample by contacting the biological sample with an agent capable of detecting a B7-4 nucleic acid molecule or polypeptide such that the presence of a B7-4 nucleic acid molecule or polypeptide is detected in the biological sample.

In another aspect, the present invention provides a method for detecting the presence of B7-4 activity in a biological sample by contacting the biological sample with an agent capable of detecting an indicator of B7-4 polypeptide activity such that the presence of the B7-4 polypeptide activity is detected in the biological sample.

In another aspect, the invention provides a method for modulating B7-4 polypeptide activity comprising contacting a cell capable of expressing B7-4 polypeptide with an agent that modulates B7-4 activity such that the B7-4 activity in the cell is modulated. In one embodiment, the agent inhibits B7-4 activity. In another embodiment, the agent stimulates B7-4 activity. In one embodiment, the agent is an antibody that binds, preferably specifically, to a B7-4 polypeptide. In another embodiment, the agent modulates expression of the B7-4 by modulating transcription of a B7-4 gene or translation of a B7-4 mRNA. In yet another embodiment, the agent is a nucleic acid molecule having a nucleotide sequence that is antisense to the coding strand of a B7-4 mRNA or a B7-4 gene.

In one embodiment, the methods of the present invention are used to treat a subject having a disorder (characterized by aberrant B7-4 polypeptide or nucleic acid expression or activity) or a condition that would benefit from modulation, either up or downmodulation, of a B7-4 molecule by administering an agent which is a B7-4 modulator to the subject. In one embodiment, the B7-4 modulator is a B7-4 polypeptide. In another embodiment the B7-4 modulator is a B7-4 nucleic acid molecule. In yet another embodiment, the B7-4 modulator is a peptide, peptidomimetic, or other small molecule. In a preferred embodiment, the disorder characterized by aberrant B7-4 polypeptide or nucleic acid expression is an immune system disorder or condition that would benefit from modulation of a B7-4 activity.

The present invention also provides a diagnostic assay for identifying the presence or absence of a genetic alteration characterized by at least one of (i) aberrant modification or mutation of a gene encoding a B7-4 polypeptide; (ii) mis-regulation of the gene; and (iii) aberrant post-translational modification of a B7-4 polypeptide, wherein a wild-type form of the gene encodes a polypeptide with a B7-4 activity.

In another aspect the invention provides a method for identifying a compound that binds to or modulates the activity of a B7-4 polypeptide. The method includes providing an indicator composition comprising a B7-4 polypeptide having B7-4 activity, respectively, contacting the indicator composition with a test compound, and determining the effect of the test compound on B7-4 activity in the indicator composition to identify a compound that modulates the activity of a B7-4 polypeptide.

In another aspect, the invention pertains to nonhuman transgenic animal that contains cells carrying a transgene encoding a B7-4 member polypeptide.

BRIEF DESCRIPTION OF THE DRAWINGS

FIG. 1 depicts the nucleotide sequence encoding a human secreted B7-4, B7-4S (SEQ ID NO: 1).

FIG. 2 depicts the nucleotide sequence encoding a human B7-4, B7-4M (SEQ ID NO: 3).

FIG. 3 depicts the amino acid sequence of human B7-4S (SEQ ID NO: 2) and illustrates the signal, IgV, IgC, and hydrophilic tail domains.

FIG. 4 depicts the amino acid sequence of human B7-4M (SEQ ID NO: 4) and illustrates the signal, IgV, IgC, and transmembrane and cytoplasmic domains.

FIG. 5 depicts the nucleotide sequence of murine B7-4 (SEQ ID NO: 10).

FIG. 6 depicts the amino acid sequence of murine B7-4 (SEQ ID NO: 11).

FIG. 7 depicts an alignment of the human B7-4M (SEQ ID NO: 4) and murine B7-4 (SEQ ID NO: 11) amino acid sequences. Identical residues are reiterated between the two sequences.

FIG. 11 illustrates that COS cells transfected with B7-4M (292) can costimulate T cell proliferation.

FIG. 12 illustrates that COS cells transfected with a B7-4M (292) can costimulate T cell proliferation.

DETAILED DESCRIPTION OF THE INVENTION

Figure 8:
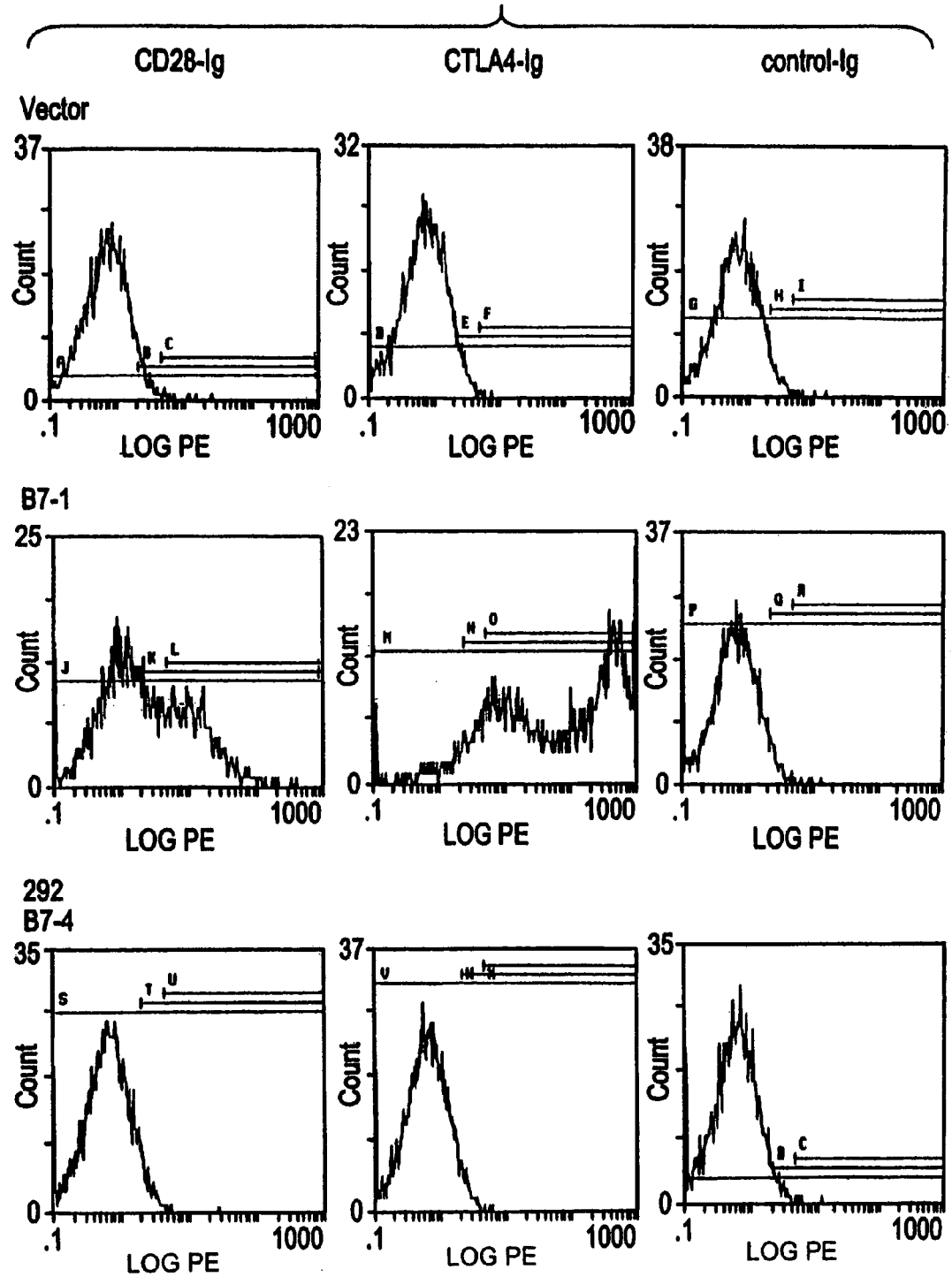
FIG. 8 illustrates the results of FACS analysis of binding of CD28Ig, CTLA4-Ig, and control Ig by B7-4M-transfected COS cells.

In addition to the previously characterized B lymphocyte activation antigens, e.g., B7-1 and B7-2, there are other antigens on the surface of antigen presenting cells (e.g., B cells, monocytes, dendritic cells, Langerhan cells, keratinocytes, endothelial cells, astrocytes, fibroblasts, oligodendrocytes) which costimulate T cells. The present invention is based, at least in part, on the discovery of novel molecules, referred to herein as B7-4 polypeptides which were isolated from keratinocyte and placental cDNA libraries and which costimulate T cells. The ability of a B7-4 polypeptide to costimulate activated T cells can be demonstrated using techniques that are known in the art, e.g., as described in WO 96/40915 or U.S. Pat. No. 5,580,756, the contents of which are incorporated herein by reference.

One embodiment of the invention features B7-4 nucleic acid molecules, preferably human B7-4 molecules, which were identified based on amino acid sequence homology to the B7 proteins. (Such families are described below).

B7-4 Nucleic Acid and Polypeptide Molecules

In one embodiment, the isolated nucleic acid molecules of the present invention encode eukaryotic protein B7-4 polypeptides. The B7-4 family of molecules share a number of conserved regions, including signal domains, IgV domains and the IgC domains. These regions are both Ig superfamily member domains and are art recognized. These domains correspond to structural units that have distinct folding patterns called Ig folds. Ig folds are comprised of a sandwich of two β sheets, each consisting of antiparallel β strands of 5–10 amino acids with a conserved disulfide bond between the two sheets in most, but not all, domains. IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than C-domains and form an additional pair of β strands.

Two novel human B7-4 molecules were identified. One form is a naturally occurring B7-4 soluble polypeptide, i.e., having a short hydrophilic domain and no transmembrane domain, and is referred to herein as B7-4S (shown in SEQ ID NO:2). One form is a cell-associated polypeptide, i.e., having a transmembrane and cytoplasmic domain, referred to herein as B7-4M (shown in SEQ ID NO:4).

B7-4 proteins comprise a signal sequence, and an IgV domain and an IgC domain. The signal sequence of SEQ ID NO:2 is shown from amino acids 1–18. The signal sequence of SEQ ID NO:4 is shown from about amino acids 1–18. The IgV domain of SEQ ID NO:2 is shown from about amino acids 19–134 and the IgV domain of SEQ ID NO:4 is shown from about amino acids 19–134. The IgC domain of SEQ ID NO:2 is shown from about amino acids 135–227 and the IgC domain of SEQ ID NO:4 is shown from about amino acids 135–227. The hydrophilic tail of the B7-4 exemplified in SEQ ID NO:2 comprises a bydrophilic tail shown from about amino acid 228–245. The B7-4 polypeptide exemplified in SEQ ID NO:4 comprises a transmembrane domain shown from about amino acids 239–259 of SEQ ID NO:4 and a cytoplasmic domain shown from about amino acids 260–290 of SEQ ID NO:4.

Murine B7-4 molecules were also identified. The murine cDNA sequence is presented in FIG. 5 and the murine B7-4 amino acid sequence is presented in FIG. 6. The present invention also pertains to these murine B7-4 molecules.

Various aspects of the invention are described in further detail in the following subsections:

I. Definitions

As used herein, the term "costimulate" with reference to activated T cells includes the ability of a molecule to provide a second, non-T cell receptor mediated, signal that induces proliferation or effector function, e.g., cytokine secretion, in a T cell that has received a T cell-receptor-mediated signal, e.g., by interaction with antigen or a polyclonal activator. Such a costimulatory signal can prevent the induction of unresponsiveness to antigen, anergy, or cell death in the T cell.

The B7-4 protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

The B7-4 molecules described herein are members of the B7 family of molecules. The term "B7 family" or "B7 molecules" as used herein includes costimulatory molecules that share sequence homology with B7 polypeptides, e.g., with B7-1, B7-2, B7-3 (recognized by the antibody BB-1), and/or B7-4. For example, human B7-1 and B7-2 share approximately 26% amino acid sequence identity when compared using the BLAST program at NCBI with the default parameters (Blosum 62 matrix with gap penalties set at existence 11 and extension 1 (See the NCBI website)).

Preferred B7 polypeptides are capable of providing costimulation to activated T cells to thereby induce T cell proliferation and/or cytokine secretion or of inhibiting costimulation of T cells, e.g., when present in soluble form. Preferred B7 family members include B7-1, B7-2, and B7-4 and soluble fragments or derivatives thereof. In one embodiment, B7 family members bind to CTLA4, CD28, ICOS, and/or other ligands on immune cells and have the ability to inhibit or induce costimulation of immune cells.

In addition, preferred B7 family members are bound by antibodies generated against one or more other B7 family members, for example, the anti-BB1 antibody recognizes B7-4 molecules.

As used herein, the term "activity" with respect to a B7-4 polypeptide includes activities which are inherent in the structure of a B7-4 protein. The term "activity" includes the ability to costimulate activated T cells and induce proliferation and/or cytokine secretion. In addition, the term "activity" includes the ability of a B7-4 polypeptide to bind its natural ligand.

As used herein, a "naturally-occurring" nucleic acid molecule refers to an RNA or DNA molecule having a nucleotide sequence that occurs in nature (e.g., encodes a natural protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g, non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized.

As used herein, the term "antibody" is intended to include immunoglobulin molecules and immunologically active portions of immunoglobulin molecules, i.e., molecules that contain an antigen binding site which binds (immunoreacts with) an antigen, such as Fab and F(ab')$_2$ fragments, single chain antibodies, scFv, Fd, or other fragments. Preferably, antibodies of the invention bind specifically or substantially specifically to B7-4 molecules. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

late the DNA or RNA molecule into an amino acid sequence. Likewise, for any B7-4-amino acid sequence, corresponding nucleotide sequences that can encode B7-4 protein can be deduced from the genetic code (which, because of its redundancy, will produce multiple nucleic acid sequences for any given amino acid sequence). Thus, description and/or disclosure herein of a B7-4 nucleotide sequence should be considered to also include description and/or

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a B7-4 polypeptide of the invention (or any portion thereof) can be use to derive the B7-4 amino acid sequence, using the genetic code to transdisclosure of the amino acid sequence encoded by the nucleotide sequence. Similarly, description and/or disclosure of a B7-4 amino acid sequence herein should be considered to also include description and/or disclosure of all possible nucleotide sequences that can encode the amino acid sequence.

II. Isolated Nucleic Acid Molecules

One aspect of the invention pertains to isolated nucleic acid molecules that encode B7-4 proteins or biologically active portions thereof, as well as nucleic acid fragments sufficient for use as hybridization probes to identify B7-4-encoding nucleic acids (e.g., B7-4 mRNA) and fragments for use as PCR primers for the amplification or mutation of B7-4 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid (i.e., sequences located at the 5' and 3' ends of the nucleic acid) in the genomic DNA of the organism from which the nucleic acid molecule is derived. For example, in various embodiments, the isolated B7-4 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. An "isolated" B7-4 nucleic acid molecule may, however, be linked to other nucleotide sequences that do not normally flank the B7-4 sequences in genomic DNA (e.g., the B7-4 nucleotide sequences may be linked to vector sequences). In certain preferred embodiments, an "isolated" nucleic acid molecule, such as a CDNA molecule, also may be free of other cellular material. However, it is not necessary for the B7-4 nucleic acid molecule to be free of other cellular material to be considered "isolated" (e.g., a B7-4 DNA molecule separated from other mammalian DNA and inserted into a bacterial cell would still be considered to be "isolated").

A nucleic acid molecule of the present invention, e.g., a nucleic acid molecule having the nucleotide sequence of SEQ ID NO:1 or 3, or a portion thereof, can be isolated using standard molecular biology techniques and the sequence information provided herein. For example, using all or a portion of the nucleic acid sequence of SEQ ID NO:1 or 3, as a hybridization probe, B7-4 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1 or 3 can be isolated by the polymerase chain reaction (PCR) using synthetic oligonucleotide primers designed based upon the sequence of SEQ ID NO:1 or 3, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to B7-4 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1 or 3.

In another preferred embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3, is one which is sufficiently complementary to the nucleotide sequence shown in SEQ ID NO:1 or 3, respectively, such that it can hybridize to the nucleotide sequence shown in SEQ ID NO:1 or 3, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the nucleotide sequence (e.g., to the entire length of the nucleotide sequence) shown in SEQ ID NO:1 or 3, or a portion of any of these nucleotide sequences.

Moreover, the nucleic acid molecule of the invention can comprise only a portion of the nucleic acid sequence of SEQ ID NO:1 or 3, for example a fragment which can be used as a probe or primer or a fragment encoding a biologically active portion of a B7-4 protein. The nucleotide sequence determined from the cloning of the B7-4 genes allows for the generation of probes and primers designed for use in identifying and/or cloning other B7-4 family members, as well as B7-4 family homologues from other species. The probe/primer typically comprises a substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3, or of a naturally occurring allelic variant or mutant of SEQ ID NO:1 or 3. In an exemplary embodiment, a nucleic acid molecule of the present invention comprises a nucleotide sequence which is at least 350, 400, 450, 500, 550, 600, 650, 700, 750, or 800 nucleotides in length and hybridizes under stringent hybridization conditions to a nucleic acid molecule of SEQ ID NO:1 or 3.

In another embodiment, a second nucleic acid molecule comprises at least about 500, 600, 700, 800, 900, or 1000 contiguous nucleotides of SEQ ID NO: 1 or SEQ ID NO: 3.

In one embodiment, a nucleic acid molecule of the invention, e.g., for use as a probe, does not include the portion of SEQ ID NO:1 from about nucleotides 815 to about 850 of SEQ ID NO:1 or about nucleotides 320 to 856 of SEQ ID NO:1. In another embodiment, a nucleic acid molecule of the invention does not include the portion of SEQ ID NO:3 from about nucleotide 314 to about 734, or from about nucleotide 835 to about 860, or from about nucleotide 1085 to about 1104 or from about nucleotide 1286 to about 1536 of SEQ ID NO:3.

In one embodiment, a nucleic acid molecule of the invention comprises at least about 500 contiguous nucleotides of SEQ ID NO:1 or SEQ ID NO:3. In a preferred embodiment, a nucleic acid molecule of the invention comprises at least about 600, at least about 700, at east about 800, at least about 900 or at least about 950 contiguous nucleotides of SEQ ID NO:1 or about 1000 contiguous nucleotides of SEQ ID NO:3. In another embodiment, a nucleic acid molecule of the invention comprises at least about 1500 or 1550 nucleotides of SEQ ID NO:3.

Preferably, an isolated nucleic acid molecule of the invention comprises at least a portion of the coding region of SEQ ID NO:1 (shown in nucleotides 59–793) or SEQ ID NO:3 (shown in nucleotides 53–922). In another embodiment, a B7-4 nucleic acid molecule comprises from about nucleotide 1 to about nucleotide 319 of SEQ ID NO:1. In another embodiment, a B7-4 nucleic acid molecule comprises from about nucleotide 855 to about nucleotide 968 of SEQ ID NO:1. In another embodiment, a B7-4 nucleic acid molecule comprises from about nucleotide 1 to about nucleotide 314 of SEQ ID NO:3. In another embodiment, a B7-4 nucleic acid molecule comprises from about nucleotide 955 to about nucleotide 1285 of SEQ ID NO:3. In another embodiment, a B7-4 nucleic acid molecule comprises from about nucleotide 1535 to about nucleotide 1552 of SEQ ID NO:3.

In other embodiments, a nucleic acid molecule of the invention has at least 70% identity, more preferably 80% identity, and even more preferably 90% identity with a nucleic acid molecule comprising: at least about 500, at least about 600, at least about 700, at east about 800, at least about 900 or at least about 1000 contiguous nucleotides of SEQ ID NO:1 or SEQ ID NO:3.

Probes based on the B7-4 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a B7-4 protein, such as by measuring a level of a B7-4-encoding nucleic acid in a sample of cells from a subject e.g., detecting B7-4 mRNA levels or determining whether a genomic B7-4 gene has been mutated or deleted.

A nucleic acid fragment encoding a "biologically active portion of a B7-4 protein" can be prepared by isolating a portion of the nucleotide sequence of SEQ ID NO:1 or 3, which encodes a polypeptide having a B7-4 biological activity (the biological activities of the B7-4 proteins are described herein), expressing the encoded portion of the B7-4 protein (e.g., by recombinant expression in vitro) and assessing the activity of the encoded portion of the B7-4 protein.

Nucleic acid molecules that differ from SEQ ID NO: 1 or 3 due to degeneracy of the genetic code, and thus encode the same a B7-4 member protein as that encoded by SEQ ID NO: 1 and 3, are encompassed by the invention. Accordingly, in another embodiment, an isolated nucleic acid molecule of the invention has a nucleotide sequence encoding a protein having an amino acid sequence shown in SEQ ID NO: 2 or SEQ ID NO:4. In another embodiment, an isolated nucleic acid molecule of the invention has a nucleotide sequence encoding a B7-4 protein.

In addition to the B7-4 nucleotide sequences shown in SEQ ID NO:1 or 3, it will be appreciated by those skilled in the art that DNA sequence polymorphisms that lead to changes in the amino acid sequences of the B7-4 proteins may exist within a population (e.g., the human population). Such genetic polymorphism in the B7-4 genes may exist among individuals within a population due to natural allelic variation. As used herein, the terms "gene" and "recombinant gene" refer to nucleic acid molecules which include an open reading frame encoding a B7-4 protein, preferably a mammalian B7-4 protein, and can further include non-coding regulatory sequences, and introns. Such natural allelic variations include both functional and non-functional B7-4 proteins and can typically result in 1–5% variance in the nucleotide sequence of a B7-4 gene. Any and all such nucleotide variations and resulting amino acid polymorphisms in B7-4 genes that are the result of natural allelic variation and that do not alter the functional activity of a B7-4 protein are intended to be within the scope of the invention.

Moreover, nucleic acid molecules encoding other B7-4 family members and, thus, which have a nucleotide sequence which differs from the B7-4 family sequences of SEQ ID NO:1 or 3 are intended to be within the scope of the invention. For example, another B7-4 cDNA can be identified based on the nucleotide sequence of human B7-4. Moreover, nucleic acid molecules encoding B7-4 proteins from different species, and thus which have a nucleotide sequence which differs from the B7-4 sequences of SEQ ID NO:1 or 3 are intended to be within the scope of the invention. For example, a mouse B7-4 cDNA can be identified based on the nucleotide sequence of a human B7-4 molecule.

Nucleic acid molecules corresponding to natural allelic variants and homologues of the B7-4 cDNAs of the invention can be isolated based on their homology to the B7-4 nucleic acids disclosed herein using the cDNAs disclosed herein, or a portion thereof, as a hybridization probe according to standard hybridization techniques. For example, a B7-4 DNA can be isolated from a human genomic DNA library using all or portion of SEQ ID NO:1 or 3 as a hybridization probe and standard hybridization techniques (e.g., as described in Sambrook, J., et al. *Molecular Cloning: A Laboratory Manual.* 2nd, ed., Cold Spring Harbor Laboratory, Cold Spring Harbor, N.Y., 1989). Moreover, a nucleic acid molecule encompassing all or a portion of a B7-4 gene can be isolated by the polymerase chain reaction using oligonucleotide primers designed based upon the sequence of SEQ ID NO: 1 or 3. For example, mRNA can be isolated from cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1 or 3. A nucleic acid molecule of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a B7-4 nucleotide sequence can be prepared by standard synthetic techniques, e.g., using an automated DNA synthesizer.

In another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiment, the nucleic acid molecule is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6x sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 or 3 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein). In addition to the B7-4 nucleotide sequences shown in SEQ ID NO: 1 and 3, it will be appreciated by those skilled in the art that DNA sequence polymorphisms that lead to minor changes in the nucleotide or amino acid sequences of a B7-4 may exist within a population. Such genetic polymorphism in a B7-4 gene may exist among individuals within a population due to natural allelic variation. Such natural allelic variations can typically result in 1–2% variance in the nucleotide sequence of the gene. Such nucleotide variations and resulting amino acid polymorphisms in a B7-4 that are the result of natural allelic variation and that do not alter the functional activity of a B7-4 polypeptide are within the scope of the invention.

In addition to naturally-occurring allelic variants of B7-4 sequences that may exist in the population, the skilled artisan will further appreciate that minor changes may be introduced by mutation into nucleotide sequences, e.g., of SEQ ID NO: 1 or 3, thereby leading to changes in the amino acid sequence of the encoded protein, without altering the functional activity of a B7-4 protein. For example, nucleotide substitutions leading to amino acid substitutions at "non-essential" amino acid residues may be made in the sequence of SEQ ID NO: 1 or 3. A "non-essential" amino acid residue is a residue that can be altered from the wild-type sequence of a B7-4 nucleic acid molecule (e.g., the sequence of SEQ ID NO: 1 or 3) without altering the functional activity of a B7-4 molecule. Exemplary residues which are non-essential and, therefore, amenable to substitution, can be identified by one of ordinary skill in the art by performing an amino acid alignment of B7 family members (or of B7-4 family members) and determining residues that are not conserved. Such residues, because they have not been conserved, are more likely amenable to substitution.

Accordingly, another aspect of the invention pertains to nucleic acid molecules encoding B7-4 proteins that contain changes in amino acid residues that are not essential for a B7-4 activity. Such B7-4 proteins differ in amino acid sequence from SEQ ID NO: 2 or 4 yet retain an inherent B7-4 activity. An isolated nucleic acid molecule encoding a non-natural variant of a B7-4 protein can be created by introducing one or more nucleotide substitutions, additions or deletions into the nucleotide sequence of SEQ ID NO: 1 or 3 such that one or more amino acid substitutions, additions or deletions are introduced into the encoded protein. Mutations can be introduced into SEQ ID NO: 1 or 3 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a B7-4 is preferably replaced with another amino acid residue from the same side chain family.

Alternatively, in another embodiment, mutations can be introduced randomly along all or part of a B7-4 coding sequence, such as by saturation mutagenesis, and the resultant mutants can be screened for their ability to bind to DNA and/or activate transcription, to identify mutants that retain functional activity. Following mutagenesis, the encoded a B7-4 mutant protein can be expressed recombinantly in a host cell and the functional activity of the mutant protein can be determined using assays available in the art for assessing a B7-4 activity.

Accordingly, another aspect of the invention pertains to nucleic acid molecules encoding B7-4 proteins that contain changes in amino acid residues that are not essential for activity.

Yet another aspect of the invention pertains to isolated nucleic acid molecules encoding a B7-4 fusion proteins. Such nucleic acid molecules, comprising at least a first nucleotide sequence encoding a B7-4 protein, polypeptide or peptide operatively linked to a second nucleotide sequence encoding a non- a B7-4 protein, polypeptide or peptide, can be prepared by standard recombinant DNA techniques.

In a preferred embodiment, a mutant B7-4 protein can be assayed for the ability to: 1) costimulate (or inhibit the costimulation of, e.g., in soluble form) the proliferation and/or effector function of activated T cells; 2) bind to an anti-B7 antibody; and/or 3) bind to a B7-4 ligand.

In addition to the nucleic acid molecules encoding B7-4 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire B7-4 coding strand, or only to a portion thereof. In one embodiment, an antisense nucleic acid molecule is antisense to a "coding region" of the coding strand of a nucleotide sequence encoding B7-4. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding B7-4. The term "noncoding region" refers to 5' and 3' sequences which flank the coding region that are not translated into amino acids (i.e., also referred to as 5' and 3' untranslated regions).

Given the coding strand sequences encoding B7-4 disclosed herein, antisense nucleic acids of the invention can be designed according to the rules of Watson and Crick base pairing. The antisense nucleic acid molecule can be complementary to the entire coding region of B7-4 mRNA, but more preferably is an oligonucleotide which is antisense to only a portion of the coding or noncoding region of B7-4 mRNA. For example, the antisense oligonucleotide can be complementary to the region surrounding the translation start site of B7-4 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a B7-4 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave B7-4 mRNA transcripts to thereby inhibit translation of B7-4 mRNA. A ribozyme having specificity for a B7-4-encoding nucleic acid can be designed based upon the nucleotide sequence of a B7-4 cDNA disclosed herein (i.e., SEQ ID NO:1 or 3). For example, a derivative of a *Tetrahymena* L-19 IVS RNA can be constructed in which the nucleotide sequence of the active site is complementary to the nucleotide sequence to be cleaved in a B7-4-encoding mRNA. See, e.g., Cech et al. U.S. Pat. No. 4,987,071; and Cech et al. U.S. Pat. No. 5,116,742. Alternatively, B7-4 mRNA can be used to select a catalytic RNA having a specific ribonuclease activity from a pool of RNA molecules. See, e.g., Bartel, D. and Szostak, J. W. (1993) *Science* 261:1411–1418.

Alternatively, B7-4 gene expression can be inhibited by targeting nucleotide sequences complementary to the regulatory region of the B7-4 (e.g., the B7-4 promoter and/or enhancers) to form triple helical structures that prevent transcription of the B7-4 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the B7-4 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of B7-4 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of B7-4 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of B7-4 can be modified, (e.g., to enhance their stability or cellular uptake), by attaching lipophilic or other helper groups to PNA, by the formation of PNA-DNA chimeras, or by the use of liposomes or other techniques of drug delivery known in the art.

For example, PNA-DNA chimeras of B7-4 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

III. Isolated B7-4 Proteins and Anti-B7-4 Antibodies

One aspect of the invention pertains to isolated B7-4 proteins, and biologically active portions thereof, as well as polypeptide fragments suitable for use as immunogens to raise anti-B7-4 antibodies. In one embodiment, native B7-4 proteins can be isolated from cells or tissue sources by an appropriate purification scheme using standard protein purification techniques. In another embodiment, B7-4 proteins are produced by recombinant DNA techniques. Alternative to recombinant expression, a B7-4 protein or polypeptide can be synthesized chemically using standard peptide synthesis techniques.

An "isolated" or "purified" protein or biologically active portion thereof is substantially free of cellular material or other contaminating proteins from the cell or tissue source from which the B7-4 protein is derived, or substantially free from chemical precursors or other chemicals when chemically synthesized. The language "substantially free of cellular material" includes preparations of B7-4 protein in which the protein is separated from cellular components of the cells from which it is isolated or recombinantly produced. In one embodiment, the language "substantially free of cellular material" includes preparations of B7-4 protein having less than about 30% (by dry weight) of non-B7-4 protein (also referred to herein as a "contaminating protein"), more preferably less than about 20% of non-B7-4 protein, still more preferably less than about 10% of non-B7-4 protein, and most preferably less than about 5% non-B7-4 protein. When the B7-4 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of B7-4 protein in which the protein is separated from chemical precursors or other chemicals which are involved in the synthesis of the protein. In one embodiment, the language "substantially free of chemical precursors or other chemicals" includes preparations of B7-4 protein having less than about 30% (by dry weight) of chemical precursors or non-B7-4 chemicals, more preferably less than about 20% chemical precursors or non-B7-4 chemicals, still more preferably less than about 10% chemical precursors or non-B7-4 chemicals, and most preferably less than about 5% chemical precursors or non-B7-4 chemicals.

Another aspect of the invention pertains to isolated B7-4 proteins. Preferably, the B7-4 proteins comprise the amino acid sequence encoded by SEQ ID NO:1 or 3. In another preferred embodiment, the protein comprises the amino acid sequence of SEQ ID NO: 2 or 4. In other embodiments, the protein has at least 50%, at least 60% amino acid identity, more preferably 70% amino acid identity, more preferably 80%, and even more preferably, 90% or 95% amino acid identity with the amino acid sequence shown in SEQ ID NO: 2 or 4.

In other embodiments, the invention provides isolated portions of a B7-4 protein. B7-4 proteins comprise a signal sequence, and an IgV domain and an IgC domain. The signal sequence of SEQ ID NO:2 is shown from amino acids 1–18. The signal sequence of SEQ ID NO:4 is shown from about amino acids 1–18. The IgV domain of SEQ ID NO:2 is shown from about amino acids 19–134 and the IgV domain of SEQ ID NO:4 is shown from about amino acids 19–134. The IgC domain of SEQ ID NO:2 is shown from about amino acids 135–227 and the IgC domain of SEQ ID NO:4 is shown from about amino acids 135–227. The hydrophilic tail of the B7-4 exemplified in SEQ ID NO:2 comprises a hydrophilic tail shown from about amino acid 228–245. The B7-4 polypeptide exemplified in SEQ ID NO:4 comprises a transmembrane domain shown from about amino acids 239–259 of SEQ ID NO:4 and a cytoplasmic domain shown from about amino acids 260–290 of SEQ ID NO:4.

The invention further pertains to soluble forms of B7-4 proteins. Such forms can be naturally occurring, e.g., as shown in SEQ ID NO:2 or can be engineered and can comprise, e.g., an extracellular domain of a B7-4 protein. Exemplary B7-4 extracellular domains comprise from about amino acids 19–238 of SEQ ID NO:4.

In one embodiment, the extracellular domain of a B7-4 polypeptide comprises the mature form of a B7-4 polypeptide, e.g., the IgV and IgC domains, but not the transmembrane and cytoplasmic domains of a B7-4 polypeptide (e.g., from about amino acid 19 to amino acid 238 of SEQ ID NO: 4) or from about amino acid 19 to amino acid 245 of SEQ. ID. NO: 2.

Biologically active portions of a B7-4 protein include peptides comprising amino acid sequences sufficiently homologous to or derived from the amino acid sequence of the B7-4 protein, which include less amino acids than the full length B7-4 proteins, and exhibit at least one activity of a B7-4 protein. Typically, biologically active portions comprise a domain or motif with at least one activity of the B7-4 protein. A biologically active portion of a B7-4 protein can be a polypeptide which is, for example, at least 10, 25, 50, 100, 150, 200 or more amino acids in length.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions×100). The percent identity between the two sequences is a function of the number of identical positions shared by the sequences, taking into account the number of gaps, and the length of each gap, which need to be introduced for optimal alignment of the two sequences. As used herein amino acid or nucleic acid "identity" is equivalent to amino acid or nucleic acid "homology".

The comparison of sequences and determination of percent identity between two sequences can be accomplished using a mathematical algorithm. In a preferred embodiment, the percent identity between two amino acid sequences is determined using the GAP program in the GCG software package (available at the Genetics Computer Group website), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the Genetics Computer Group website), using a NWSgapdna.CMP matrix and a gap weight of 40, 50, 60, 70, or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to B7-4 or PD-1 nucleic acid molecules of the invention. BLAST protein searches can be performed with the XBLAST program, score=50, wordlength=3 to obtain amino acid sequences homologous to B7-4 or PD-1 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. For example, the nucleotide sequences of the invention were analyzed using the default Blastn matrix 1-3 with gap penalties set at: existence 11 and extension 1. The amino acid sequences of the invention were analyzed using the default settings: the Blosum 62 matrix with gap penalties set at existence 11 and extension 1. See the NCBI website.

The invention also provides B7-4 chimeric or fusion proteins. As used herein, a B7-4 "chimeric protein" or "fusion protein" comprises a B7-4 polypeptide operatively linked to a non-B7-4 polypeptide. An "B7-4 polypeptide" refers to a polypeptide having an amino acid sequence corresponding to B7-4 polypeptide, whereas a "non-B7-4 polypeptide" refers to a polypeptide having an amino acid sequence corresponding to a protein which is not substantially homologous to the B7-4 protein, e.g., a protein which is different from the B7-4 protein and which is derived from the same or a different organism. Within a B7-4 fusion protein the B7-4 polypeptide can correspond to all or a portion of a B7-4 protein. In a preferred embodiment, a B7-4 fusion protein comprises at least one biologically active portion of a B7-4 protein, e.g., an extracellular domain of a B7-4 protein. Within the fusion protein, the term "operatively linked" is intended to indicate that the B7-4 polypeptide and the non-B7-4 polypeptide are fused in-frame to each other. The non-B7-4 polypeptide can be fused to the N-terminus or C-terminus of the B7-4 polypeptide.

For example, in one embodiment, the fusion protein is a GST-B7-4 member fusion protein in which the B7-4 member sequences are fused to the C-terminus of the GST sequences. In another embodiment, the fusion protein is a B7-4 member-HA fusion protein in which the B7-4 member nucleotide sequence is inserted in a vector such as pCEP4-HA vector (Herrscher, R. F. et al. (1995) *Genes Dev.* 9:3067–3082) such that the B7-4 member sequences are fused in frame to an influenza hemagglutinin epitope tag. Such fusion proteins can facilitate the purification of a recombinant B7-4 member.

A B7-4 fusion protein can be produced by recombinant expression of a nucleotide sequence encoding a first peptide having B74 activity and a nucleotide sequence encoding second peptide corresponding to a moiety that alters the solubility, affinity, stability or valency of the first peptide, for example, an immunoglobulin constant region. Preferably, the first peptide consists of a portion of the of a B7-4 polypeptide (e.g., a portion of amino acid residues 1–238 or 19–238 (after cleavage of the signal sequence) of the sequence shown in SEQ ID NO:4 that is sufficient to costimulate activated T cells. The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964, 5,580,756, 5,844,095 and the like, incorporated herein by reference). A resulting B7-4-Ig fusion protein may have altered B7-4 solubility, binding affinity, stability and/or valency (i.e., the number of binding sites available per molecule) and may increase the efficiency of protein purification. Fusion proteins and peptides produced by recombinant techniques may be secreted and isolated from a mixture of cells and medium containing the protein or peptide. Alternatively, the protein or peptide may be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Particularly preferred B7-4 Ig fusion proteins include the extracellular domain portion or variable region-like domain of a human B7-4 coupled to an immunoglobulin constant region. The immunoglobulin constant region may contain genetic modifications which reduce or eliminate effector activity inherent in the immunoglobulin structure. For example, DNA encoding the extracellular portion of a B7-4 polypeptide can be joined to DNA encoding the hinge, CH2 and CH3 regions of human IgCγ1 and/or IgCγ4 modified by site directed mutagenesis, e.g., as taught in WO 97/28267.

Preferably, a B7-4 fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A B7-4 encoding nucleic acid can be cloned into such an expression vector such that the fusion moiety is linked in-frame to the B7-4 protein.

In another embodiment, the fusion protein is a B7-4 protein containing a heterologous signal sequence at its N-terminus. In certain host cells (e.g., mammalian host cells), expression and/or secretion of B7-4 can be increased through use of a heterologous signal sequence.

The B7-4 fusion proteins of the invention can be incorporated into pharmaceutical compositions and administered to a subject in vivo. Use of B7-4 fusion proteins may be useful therapeutically for the treatment of immunological disorders, e.g., autoimmune diseases or in the case of transplantation. Moreover, the B7-4-fusion proteins of the invention can be used as immunogens to produce anti-B7-4 antibodies in a subject, to purify B7-4 ligands and in screening assays to identify molecules which inhibit the interaction of B7-4 with a B7-4 ligand.

Preferably, a B7-4 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A B7-4-encoding nucleic acid can be cloned into such an expression vector such that the fusion moiety is linked in-frame to the B7-4 protein.

The present invention also pertains to variants of the B7-4 proteins which function as either B7-4 agonists (mimetics) or as B7-4 antagonists. Variants of the B7-4 proteins can be generated by mutagenesis, e.g., discrete point mutation or truncation of a B7-4 protein. An agonist of the B7-4 proteins can retain substantially the same, or a subset, of the biological activities of the naturally occurring form of a B7-4 protein. An antagonist of a B7-4 protein can inhibit one or more of the activities of the naturally occurring form of the B7-4 protein by, for example, competitively modulating a cellular activity of a B7-4 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the B7-4 protein.

In one embodiment, variants of a B7-4 protein which function as either B7-4 agonists (mimetics) or as B7-4 antagonists can be identified by screening combinatorial libraries of mutants, e.g., truncation mutants, of a B7-4 protein for B7-4 protein agonist or antagonist activity. In one embodiment, a variegated library of B7-4 variants is generated by combinatorial mutagenesis at the nucleic acid level and is encoded by a variegated gene library. A variegated library of B7-4 variants can be produced by, for example, enzymatically ligating a mixture of synthetic oligonucleotides into gene sequences such that a degenerate set of potential B7-4 sequences is expressible as individual polypeptides, or alternatively, as a set of larger fusion proteins (e.g., for phage display) containing the set of B7-4 sequences therein. There are a variety of methods which can be used to produce libraries of potential B7-4 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential B7-4 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a B7-4 protein coding sequence can be used to generate a variegated population of B7-4 fragments for screening and subsequent selection of variants of a B7-4 protein. In one embodiment, a library of coding sequence fragments can be generated by treating a double stranded PCR fragment of a B7-4 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the B7-4 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of B7-4 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify B7-4 variants (Arkin and Youvan (1992) *Proc. Natl. Acad. Sci. USA* 89:7811–7815; Delagrave et al. (1993) *Protein Engineering* 6(3):327–331).

In one embodiment, cell based assays can be exploited to analyze a variegated B7-4 library. For example, a library of expression vectors can be transfected into a cell line which ordinarily synthesizes and secretes B7-4. The transfected cells are then cultured such that B7-4 and a particular mutant B7-4 are secreted and the effect of expression of the mutant on B7-4 activity in cell supernatants can be detected, e.g., by any of a number of enzymatic assays. Plasmid DNA can then be recovered from the cells which score for inhibition, or alternatively, potentiation of B7-4 activity, and the individual clones further characterized.

An isolated B7-4 protein, or a portion or fragment thereof, can be used as an immunogen to generate antibodies that bind B7-4 using standard techniques for polyclonal and monoclonal antibody preparation. A full-length B7-4 protein can be used or, alternatively, the invention provides antigenic peptide fragments of B7-4 for use as immunogens. The antigenic peptide of B7-4 comprises at least 8 amino acid residues and encompasses an epitope of B7-4 such that an antibody raised against the peptide forms a specific immune complex with B7-4. Preferably, the antigenic peptide comprises at least 10 amino acid residues, more preferably at least 15 amino acid residues, even more preferably at least 20 amino acid residues, and most preferably at least 30 amino acid residues.

Alternatively, an antigenic peptide fragment of a B7-4 polypeptide can be used as the immunogen. An antigenic peptide fragment of a B7-4 polypeptide typically comprises at least 8 amino acid residues of the amino acid sequence shown in SEQ ID NO: 2 or 4 and encompasses an epitope of a B7-4 polypeptide such that an antibody raised against the peptide forms an immune complex with a B7-4 molecule. Preferred epitopes encompassed by the antigenic peptide are regions of B7-4 that are located on the surface of the protein, e.g., hydrophilic regions. In one embodiment, an antibody binds substantially specifically to a B7-4 molecule. In another embodiment, an antibody binds specifically to a B7-4 polypeptide.

Preferably, the antigenic peptide comprises at least about 10 amino acid residues, more preferably at least about 15 amino acid residues, even more preferably at least 20 about amino acid residues, and most preferably at least about 30 amino acid residues. Preferred epitopes encompassed by the antigenic peptide are regions of a B7-4 polypeptide that are located on the surface of the protein, e.g., hydrophilic regions, and that are unique to a B7-4 polypeptide. In one embodiment such epitopes can be specific for a B7-4 proteins from one species, such as mouse or human (i.e., an antigenic peptide that spans a region of a B7-4 polypeptide that is not conserved across species is used as immunogen; such non conserved residues can be determined using an alignment such as that provided herein). A standard hydrophobicity analysis of the B7-4 protein can be performed to identify hydrophilic regions.

A B7-4 immunogen typically is used to prepare antibodies by immunizing a suitable subject, (e.g., rabbit, goat, mouse or other mammal) with the immunogen. An appropriate immunogenic preparation can contain, for example, a recombinantly expressed B7-4 protein or a chemically synthesized B7-4 peptide. The preparation can further include an adjuvant, such as Freund's complete or incomplete adjuvant, or similar immunostimulatory agent. Immunization of a suitable subject with an immunogenic B7-4 preparation induces a polyclonal anti-B7-4 antibody response.

Accordingly, another aspect of the invention pertains to anti-B7-4 antibodies. Polyclonal anti-B7-4 antibodies can be prepared as described above by immunizing a suitable subject with a B7-4 immunogen. The anti-B7-4 antibody titer in the immunized subject can be monitored over time by standard techniques, such as with an enzyme linked immunosorbent assay (ELISA) using immobilized a B7-4 polypeptide. If desired, the antibody molecules directed against a B7-4 polypeptide can be isolated from the mammal (e.g., from the blood) and further purified by well known techniques, such as protein A chromatography to obtain the IgG fraction. At an appropriate time after immunization, e.g., when the anti-B7-4 antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J Biol Chem* 255:4980–83; Yeh etal. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a B7-4 immunogen as described above, and the culture supernatants of the resulting hybridoma cells are screened to identify a hybridoma producing a monoclonal antibody that binds specifically to a B7-4 polypeptide.

Any of the many well known protocols used for fusing lymphocytes and immortalized cell lines can be applied for the purpose of generating an anti-B7-4 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a B7-4 molecule, e.g., using a standard ELISA assay.

As an alternative to preparing monoclonal antibody-secreting hybridomas, a monoclonal anti-B7-4 antibody can be identified and isolated by screening a recombinant combinatorial immunoglobulin library (e.g., an antibody phage display library) with a B7-4 to thereby isolate immunoglobulin library members that bind a B7-4 polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et aL International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al. (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Additionally, recombinant anti-B7-4 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al European Patent Application 173,494; Neuberger et al. PCT Application WO 86/01533; Cabilly et al. U.S. Pat. No. 4,816,567; Cabilly et al. European Patent Application 125,023; Better et al (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable geneic display package and vectors containing nucleic acid molecules encoding a second polypeptide chain of a single binding pair member using techniques known in the art, e.g., as described in U.S. Pat. Nos. 5,565,332, 5,871,907, or 5,733,743.

An anti-B7-4 antibody (e.g., monoclonal antibody) can be used to isolate a B7-4 polypeptide by standard techniques, such as affinity chromatography or immunoprecipitation. Anti-B7-4 antibodies can facilitate the purification of natural B7-4 polypeptides from cells and of recombinantly produced B7-4 polypeptides expressed in host cells. Moreover, an anti-B7-4 antibody can be used to detect a B7-4 protein (e.g., in a cellular lysate or cell supernatant). Detection may be facilitated by coupling (i.e., physically linking) the antibody to a detectable substance. Accordingly, in one embodiment, an anti-B7-4 antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

Yet another aspect of the invention pertains to anti-B7-4 antibodies that are obtainable by a process comprising:

(a) immunizing an animal with an immunogenic B7-4 protein, or an immunogenic portion thereof unique to a B7-4 polypeptide; and (b) isolating from the animal antibodies that specifically bind to a B7-4 protein.

IV. Recombinant Expression Vectors and Host Cells

Another aspect of the invention pertains to vectors, preferably expression vectors, containing a nucleic acid encoding a B7-4 family protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., B7-4 family proteins, mutant forms of B7-4 proteins, fusion proteins, and the like).

The recombinant expression vectors of the invention can be designed for expression of B7-4 proteins in prokaryotic or eukaryotic cells. For example, B7-4 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in B7-4 activity assays, (e.g., direct assays or competitive assays described in detail below), or to generate antibodies specific for B7-4 proteins, for example.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the B7-4 expression vector is a yeast expression vector. Examples of vectors for expression in yeast *S. cerivisae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corp, San Diego, Calif.).

Alternatively, B7-4 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryoiic and eukaryotic cells see chapters 16 and 17 of Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Alternatively, a B7-4 polypeptide can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156–2165) and the pVL series (Lucklow, V. A., and Summers, M. D., (1989) *Virology* 170:31–39).

In yet another embodiment, a nucleic acid molecule of the invention is expressed in mammalian cells using a mammalian expression vector. Examples of mammalian expression vectors include pMex-NeoI, pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40.

Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response*, e.d. Nouer, L., CRC, Boca Raton, Fla., pp 167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604; and PCT Publication No. WO 93/23431), FK506-related molecules (see e.g, PCT Publication No. WO 94/18317) or tetracyclines (Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313). Accordingly, in another embodiment, the invention provides a recombinant expression vector in which a B7-4 DNA is operatively linked to an inducible eukaryotic promoter, thereby allowing for inducible expression of a B7-4 protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to B7-4 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a B7-4 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a B7-4 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a B7-4 protein. Accordingly, the invention further provides methods for producing a B7-4 protein using the host cells of the invention. In one embodiment, the method comprises culturing the host cell of invention (into which a recombinant expression vector encoding a B7-4 protein has been introduced) in a suitable medium such that a B7-4 protein is produced. In another embodiment, the method further comprises isolating a B7-4 protein from the medium or the host cell.

Certain host cells of the invention can also be used to produce non-human transgenic animals. For example, in one embodiment, a host cell of the invention is a fertilized oocyte or an embryonic stem cell into which B7-4-coding sequences have been introduced. Such host cells can then be used to create non-human transgenic animals in which exogenous B7-4 sequences have been introduced into their genome or homologous recombinant animals in which endogenous B7-4 sequences have been altered. Such animals are useful for studying the function and/or activity of a B7-4 polypeptide and for identifying and/or evaluating modulators of B7-4 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous B7-4 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a B7-4-encoding nucleic acid into the male pronucleus of a fertilized oocyte, e.g., by microinjection, retroviral infection, and allowing the oocyte to develop in a pseudopregnant female foster animal. The B7-4 cDNA sequence of SEQ ID NO:1 or 3 can be introduced as a transgene into the genome of a non-human animal. Alternatively, a nonhuman homologue of a human B7-4 gene, such as a mouse or rat B7-4 gene, can be used as a transgene. Alternatively, a B7-4 gene bomologue, such as another B7-4 family member, can be isolated based on hybridization to the B7-4 family cDNA sequences of SEQ ID NO:1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to a B7-4 transgene to direct expression of a B7-4 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a B7-4 transgene in its genome and/or expression of B7-4 mRNA in tissues or cells of the animals. A transgenic founder animal can then be used to breed additional animals carrying the transgene. Moreover, transgenic animals carrying a transgene encoding a B7-4 protein can further be bred to other transgenic animals carrying other transgenes.

To create a homologous recombinant animal, a vector is prepared which contains at least a portion of a B7-4 gene into which a deletion, addition or substitution has been introduced to thereby alter, e.g., functionally disrupt, the B7-4 gene. The B7-4 gene can be a human gene (e.g., the SEQ ID NO:1 or 3), but more preferably, is a non-human homologue of a human B7-4 gene (e.g., a cDNA isolated by stringent hybridization with the nucleotide sequence of SEQ ID NO:1 or 3). For example, a mouse B7-4 gene can be used to construct a homologous recombination vector suitable for altering an endogenous B7-4 gene in the mouse genome. In a preferred embodiment, the vector is designed such that, upon homologous recombination, the endogenous B7-4 gene is functionally disrupted (i.e., no longer encodes a functional protein; also referred to as a "knock out" vector). Alternatively, the vector can be designed such that, upon homologous recombination, the endogenous B7-4 gene is mutated or otherwise altered but still encodes a functional protein (e.g., the upstream regulatory region can be altered to thereby alter the expression of the endogenous B7-4 protein). In the homologous recombination vector, the altered portion of the B7-4 gene is flanked at its 5' and 3' ends by additional nucleic acid sequence of the B7-4 gene to allow for homologous recombination to occur between the exogenous B7-4 gene carried by the vector and an endogenous B7-4 gene in an embryonic stem cell. The additional flanking B7-4 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced B7-4 gene has homologously recombined with the endogenous B7-4 gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nuc. Acids Res.* 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet.* 13:367–375; and Fiering, S. et al. (1 993) *Proc. Natl. Acad. Sci. USA* 90:8469–8473). Tetracycline-regulated inducible homologous recombination systems, such as described in PCT Publication No. WO 94/29442 and PCT Publication No. WO 96/01313, also can be used.

For example, in another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

V. Pharmaceutical Compositions

B7-4 modulators ("active compounds") of the invention (e.g., B7-4 inhibitory or stimulatory agents, including B7-4 nucleic acid molecules, proteins, antibodies, or compounds identified as modulators of a B7-4 activity) can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a B7-4 protein or anti-B7-4 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) methods of treatment, e.g., up- or down-modulating the immune response; b) screening assays; c) predictive medicine (e.g., diagnostic assays, prognostic assays, monitoring clinical trials, and pharmacogenetics). The isolated nucleic acid molecules of the invention can be used, for example, to express B7-4 protein (e.g., via a recombinant expression vector in a host cell in gene therapy applications), to detect B7-4 mRNA (e.g., in a biological sample) or a genetic alteration in a B7-4 gene, and to modulate B7-4 activity, as described further below. The B7-4 proteins can be used to treat disorders characterized by insufficient or excessive production of B7-4 inhibitors. In addition, the B7-4 proteins can be used to screen for naturally occurring B7-4 ligands, to screen for drugs or compounds which modulate B7-4 activity, as well as to treat disorders characterized by insufficient or excessive production of B7-4 protein or production of B7-4 protein forms which have decreased or aberrant activity compared to B7-4 wild type protein. Moreover, the anti-B7-4 antibodies of the invention can be used to detect and isolate B7-4 proteins, regulate the bioavailability of B7-4 proteins, and modulate B7-4 activity e.g., modulate immune responses.

A. Methods of Treatment:

The present invention provides for both prophylactic and therapeutic methods of treating a subject at risk of (or susceptible to) a disorder or having a disorder associated with aberrant B7-4 expression or activity.

1. Prophylactic Methods

In one aspect, the invention provides a method for preventing in a subject, a disease or condition associated with an aberrant B7-4 expression or activity, by administering to the subject a B7-4 polypeptide or an agent which modulates B7-4 polypeptide expression or at least one B7-4 activity. Subjects at risk for a disease which is caused or contributed to by aberrant B7-4 expression or activity can be identified by, for example, any or a combination of diagnostic or prognostic assays as described herein. Administration of a prophylactic agent can occur prior to the manifestation of symptoms characteristic of B7-4 aberrancy, such that a disease or disorder is prevented or, alternatively, delayed in its progression. Depending on the type of B7-4 aberrancy or condition, for example, a B7-4 polypeptide, B7-4 agonist or B7-4 antagonist agent can be used for treating the subject. The appropriate agent can be determined based on screening assays described herein.

2. Therapeutic Methods

Another aspect of the invention pertains to methods of modulating B7-4 expression or activity for therapeutic purposes. Accordingly, in an exemplary embodiment, the modulatory method of the invention involves contacting a cell with a B7-4 polypeptide or agent that modulates one or more of the activities of B7-4 protein activity associated with the cell. An agent that modulates B7-4 protein activity can be an agent as described herein, such as a nucleic acid or a protein, a naturally-occurring target molecule of a B7-4 protein (e.g., a B7-4 ligand), a B7-4 antibody, a B7-4 agonist or antagonist, a peptidomimetic of a B7-4 agonist or antagonist, or other small molecule. In one embodiment, the agent stimulates one or more B7-4 activities. Examples of such stimulatory agents include active B7-4 protein and a nucleic acid molecule encoding B7-4 polypeptide that has been introduced into the cell. In another embodiment, the agent inhibits one or more B7-4 activities. Examples of such inhibitory agents include antisense B7-4 nucleic acid molecules, anti-B7-4 antibodies soluble forms of B7-4 molecules, and B7-4 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder that would benefit from modulation of a B7-4 protein, e.g., a disorder which would benefit from up or downrnodulation of the immune response, or which is characterized by aberrant expression or activity of a B7-4 protein or nucleic acid molecule. In one embodiment, the method involves administering an agent (e.g., an agent identified by a screening assay described herein), or combination of agents that modulates (e.g., upregulates or downregulates) B7-4 expression or activity. In another embodiment, the method involves administering a B7-4 protein or nucleic acid molecule as therapy to compensate for reduced or aberrant B7-4 expression or activity.

Stimulation of B7-4 activity is desirable in situations in which B7-4 is abnormally downregulated and/or in which increased B7-4 activity is likely to have a beneficial effect. Likewise, inhibition of B7-4 activity is desirable in situations in which B7-4 is abnormally upregulated and/or in which decreased B7-4 activity is likely to have a beneficial effect.

3. Downregulation of Immune Responses

It is possible to downregulate the function of a B7-4 polypeptide, and thereby downregulate immune responses, in a number of ways. Downregulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen where the reexposure occurs in the absence of the tolerizing agent.

For example, B7-4 polypeptides, (including soluble, monomeric forms of a B7-4 polypeptide) or a B7-4 fusion protein, (e.g., a B7-4-Ig), and anti-B7-4 antibodies that fail to deliver a costimulatory signal to T cells that have received a primary activation signal, can be used to block B7-4 ligand(s) on T cells and thereby provide a specific means by which to cause immunosuppression and/or induce tolerance in a subject. Such blocking or inhibitory forms of B7-4 polypeptides and fusion proteins and blocking antibodies can be identified by their ability to inhibit T cell proliferation and/or cytokine production when added to an in vitro costimulation assay as previously described herein. In contrast to the monomeric form, forms of a B7-4 polypeptide, such as an intact cell surface a B7-4 polypeptide, preferably transmit a costimulatory signal to the T cells, resulting in an increased secretion of cytokines when compared to activated T cells that have not received a costimulatory signal.

In one embodiment, fusion proteins comprising a B7-4 first peptide fused to a second peptide having an activity of another B lymphocyte antigen (e.g., B7-1 or B7-2) can be used to modify T cell mediated immune responses. Alternatively, two separate peptides having an activity of B lymphocyte antigens, (for example, a B7-4 polypeptide with B7-2 and/or B7-1), or a combination of blocking antibodies (e.g., antibodies against a B7-4 polypeptide with anti-B7-2 and/or anti-B7-1 monoclonal antibodies) can be combined as a single composition or administered separately (simultaneously or sequentially), to upregulate or downregulate T cell mediated immune responses in a subject. Furthermore, a therapeutically active amount of one or more peptides having a B7-4 polypeptide activity, with B7-1 and/or B7-1 activity can be used in conjunction with other immunomodulating reagents to influence immune responses. Examples of other immunomodulating reagents include blocking antibodies, (e.g., against CD28, CTLA4, and/or ICOS, or against other T cell markers, or against cytokines), fusion proteins (e.g., CTLA4Ig), or immunosuppressive drugs, (e.g., rapamycin, cyclosporine A or FK506).

The peptides produced from the nucleic acid molecules of the present invention may also be useful in the construction of therapeutic agents which block T cell function by destruction of the T cell. For example, as described, naturally occurring secreted forms of a B7-4 polypeptide can be used. Alternatively, such secreted forms can be constructed by standard genetic engineering techniques. By linking a soluble form of a B7-4 polypeptide to a toxin such as ricin, an agent capable of preventing T cell activation can be made. Infusion of one or a combination of immunotoxins, (e.g., B7-4-ricin with B7-2-ricin and/or B7-1-ricin), into a patient may result in the death of T cells, particularly of activated T cells that express higher amounts of CD28 and CTLA4.

Soluble forms of a B7-4 polypeptide in a monovalent form alone may be useful in blocking a B7-4 polypeptide function, as described above, in which case a carrier molecule may also be employed.

Another method of preventing the function of a B7-4 polypeptide is through the use of an antisense or triplex oligonucleotide. For example, an oligonucleotide complementary to the area around a B7-4 polypeptide translation initiation site, can be synthesized. One or more antisense oligonucleotides can be added to cell media, typically at 200 µg/ml, or administered to a patient to prevent the synthesis of a B7-4 polypeptide. The antisense oligonucleotide is taken up by cells and hybridizes to a B7-4 mRNA to prevent translation. Alternatively, an oligonucleotide which binds double-stranded DNA to form a triplex construct to prevent DNA unwinding and transcription can be used. As a result of either, synthesis of a B7-4 polypeptide is blocked.

Downregulating or preventing one or more B7-4 polypeptide functions, e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a B7-4 polypeptide alone or in conjunction with a monomeric form of a different B7 peptide (e.g., B7-1, B7-2) or blocking antibody), prior to transplantation can lead to the binding of the molecule to the natural ligand(s) on the immune cells without transmitting the corresponding costimulatory signal. Blocking B lymphocyte antigen function in this manner prevents cytokine synthesis by immune cells, such as T cells and, thus, acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens. For example, it may be desirable to block the function of B7-1 and B7-4, B7-2 and B7-4, or B7-1 and B7-2 and a B7-4 polypetide, by administering a soluble form of a combination of peptides having an activity of each of these antigens or blocking antibodies against these antigens (separately or together in a single composition) prior to transplantation. Alternatively, inhibitory forms of B7-4 polypeptides can be used with other suppressive agents such as blocking antibodies against other T cell markers or against cytokines, other fusion proteins, e.g., CTLA4Ig, or immunosuppressive drugs.

The efficacy of particular blocking reagents in preventing organ transplant rejection or GVHD can be assessed using animal models that are predictive of efficacy in humans. Because B7 polypeptides display amino acid conservation across species, it is likely that other B7-4 antigens can function across species, thereby allowing use of reagents composed of human proteins in animal systems. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., *Science,* 257: 789–792 (1992) and Turka et al., *Proc. Natl. Acad. Sci. USA,* 89: 11102–11105 (1992). In addition, murine models of GVHD (see Paul ed., *Fundamental Immunology*, Raven Press, New York, 1989, pp. 846–847) can be used to determine the effect of blocking function of a B7-4 polypeptide in vivo on the development of that disease.

Blocking a B7-4 polypeptide function, e.g., by use of a peptide having a B7-4 polypeptide activity alone or in combination with a peptide having B7-1 activity and/or a peptide having B7-2 activity, may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

The IgE antibody response in atopic allergy is highly T cell dependent and, thus, inhibition of B lymphocyte antigen induced T cell activation may be useful therapeutically in the treatment of allergy and allergic reactions. An inhibitory form of a B7-4 protein, such as a peptide having a B7-4 polypeptide activity alone or in combination with another B lymphocyte antigen, such as B7-1 or B7-2, can be administered to an allergic subject to inhibit T cell mediated allergic responses in the subject. Inhibition of B7-4 costimulation of T cells may be accompanied by exposure to allergen in conjunction with appropriate MHC molecules. Allergic reactions may be systemic or local in nature, depending on the route of entry of the allergen and the pattern of deposition of IgE on mast cells or basophils. Thus, it may be necessary to inhibit T cell mediated allergic responses locally or systemically by proper administration of an inhibitory form of a B7-4 protein.

Inhibition of T cell activation through blockage of a B7-4 antigen function may also be important therapeutically in viral infections of T cells. For example, in the acquired immune deficiency syndrome (AIDS), viral replication is stimulated by T cell activation. Blocking a B7-4 function could lead to a lower level of viral replication and thereby ameliorate the course of AIDS. In addition, it may also be desirable to block the function of a combination of B lymphocyte antigens i.e., B7-4 with B7-2 and/or B7-1.

4. Upregulation of Immune Responses

Upregulation of a B lymphocyte antigen function, as a means of upregulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection.

Viral infections are cleared primarily by cytolytic T cells. In accordance with the present invention, it is believed that B7-4 polypeptide interacting with their natural ligand(s) on T cells may result in an increase in the cytolytic activity of at least some T cells. The addition of a soluble B7-4 peptide, alone, or in combination with a different B7-polypeptide, in a multi-valent form, to stimulate T cell activity through the costimulation pathway would thus be therapeutically useful in situations where more rapid or thorough clearance of virus would be beneficial. These would include viral skin diseases such as Herpes or shingles, in which cases the multi-valent soluble B7-4 polypeptide or combination of such peptide with a peptide having B7-1 activity and/or a peptide having B7-2 activity is delivered topically to the skin. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a B7-4 peptide (alone or in combination with a peptide having B7-1 activity and/or a peptide having B7-2 activity) or together with a stimulatory form of a soluble B7-4 peptide (alone or in combination with a peptide having B7-1 activity and/or a peptide having B7-2 activity) and reintroducing the in vitro activated T cells into the patient. Another method of enhancing anti-viral immune responses would be to isolate infected cells from a patient, transfect them with a nucleic acid molecule encoding a peptide having the activity of a B lymphocyte antigen as described herein such that the cells express all or a portion of a B7-4 antigen on their surface, and reintroduce the transfected cells into the patient. The infected cells would now be capable of delivering a costimulatory signal to, and thereby activate, T cells in vivo.

Stimulatory forms of B lymphocyte antigens may also be used prophylactically in vaccines against various pathogens. Immunity against a pathogen, e.g., a virus, could be induced by vaccinating with a viral protein along with a stimulatory form of a B7-4 polypeptide in an appropriate adjuvant. Alternately, an expression vector which encodes genes for both a pathogenic antigen and a peptide having the activity of a B7-4 antigen, e.g., a vaccinia virus expression vector engineered to express a nucleic acid molecule encoding a viral protein and a nucleic acid molecule encoding a B7-4 polypeptide as described herein, can be used for vaccination. DNA vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. 1996. *J. Biotechnol.* 44:37)). Alternatively, DNA vaccines can be administered by non-invasive means. For example, pure or lipid-formulated DNA can be delivered to the respiratory system or targeted elsewhere, e.g., Peyers patches by oral delivery of DNA (Schubert. 1997. *Proc. Natl. Acad. Sci. USA* 94:961). Attenuated microorganisms can be used for delivery to mucosal surfaces. (Sizemore et al. 1995. *Science.* 270:29)

Presentation of a B7-4 polypeptide with class I MHC proteins by, for example, a cell transfected to coexpress a B7-4 polypeptide and MHC class I α chain protein and $\beta_2$ microglobulin may also result in activation of cytolytic CD8+ T cells and provide immunity from viral infection. Pathogens for which vaccines may be useful include hepatitis B, hepatitis C, Epstein-Barr virus, cytomegalovirus, HIV-1, HIV-2, tuberculosis, malaria and schistosomiasis.

In another application, upregulation or enhancement of B lymphocyte antigen function may be useful in the induction of tumor immunity. Tumor cells (e.g., sarcoma, melanoma, lymphoma, leukemia, neuroblastoma, carcinoma) transfected with a nucleic acid encoding at least one B7-4 antigen can be administered to a subject to overcome tumor-specific tolerance in the subject. If desired, the tumor cell can be transfected to express a combination of B7 polypeptides (e.g., B7-1, B7-2, B7-4). For example, tumor cells obtained from a patient can be transfected ex vivo with an expression vector directing the expression of a B7-4 polypeptide alone, or in conduction with a peptide having B7-1 activity and/or B7-2 activity. The transfected tumor cells are returned to the patient to result in expression of the peptides on the surface of the transfected cell. Alternatively, gene therapy techniques can be used to target a tumor cell for transfection in vivo.

The presence of the peptide having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to express sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-4) induces a T cell mediated immune response against the transfected tumor cell. Optionally, a gene encoding an antisense construct which blocks expression of an MHC class II associated protein, such as the invariant chain, can also be cotransfected with a DNA encoding a B7-4 polypeptide to promote presentation of tumor associated antigens and induce tumor specific immunity. Expression of B7-1 by B7 negative murine tumor cells has been shown to induce T cell mediated specific immunity accompanied by tumor rejection and prolonged protection to tumor challenge in mice (Chen, L., et al. (1992) *Cell* 71, 1093–1102; Townsend, S. E. and Allison, J. P. (1993) *Science* 259, 368–370; Baskar, S., et al. (1993) *Proc. Natl. Acad. Sci.* 90, 5687–5690). Thus, the induction of a T cell mediated immune response in a human subject may be sufficient to overcome tumor-specific tolerance in the subject.

In another embodiment, a stimulatory form of one or more B7-4 peptides (e.g., expressed on a cell surface) can be administered to a tumor-bearing patient to provide a costimulatory signal to T cells in order to induce anti-tumor immunity using techniques that are known in the art.

In yet another embodiment, the production of an inhibitory form of a B7-4 molecule can be inhibited, e.g., using antisense RNA, in order to upregulate the immune response. For example, in one embodiment, the production of inhibitory B7-4 molecules by a tumor cell can be inhibited in order to increase anti-tumor immunity.

In a specific embodiment, T cells are obtained from a subject and cultured ex vivo to expand the population of T cells. In a further embodiment the T cells are then administered to a subject. T cells can be stimulated to proliferate in vitro by, for example, providing to the T cells a primary activation signal and a costimulatory signal, as is known in the art. Various forms of B7-4 proteins can also be used to costimulate proliferation of T cells. In one embodiment T cells are cultured ex vivo according to the method described in PCT Application No. WO 94/29436. The costimulatory molecule can be soluble, attached to a cell membrane or attached to a solid surface, such as a bead.

B. Identification of Cytokines Induced by B7-4 Mediated Costimulation

The B7-4 molecules as described herein can be used to identify cytokines which are produced by T cells in response to stimulation by a B7-4 polypeptide. T cells can be suboptimally stimulated in vitro with a primary activation signal, such as phorbol ester, anti-CD3 antibody or preferably antigen in association with an MHC class II molecule, and given a costimulatory signal by a stimulatory form of B7-4 antigen, for instance by a cell transfected with nucleic acid encoding a B7-4 polypeptide and expressing the peptide on its surface or by a soluble, stimulatory form of the peptide. Known cytokines released into the media can be identified by ELISA or by the ability of an antibody which blocks the cytokine to inhibit T cell proliferation or proliferation of other cell types that is induced by the cytokine. An IL-4 ELISA kit is available from Genzyme (Cambridge Mass.), as is an IL-7 blocking antibody. Blocking antibodies against IL-9 and IL-12 are available from Genetics Institute (Cambridge, Mass.).

An in vitro T cell costimulation assay as described above can also be used in a method for identifying novel cytokines which may be induced by costimulation. For example, where stimulation of the CD28/CTLA4 pathway seems to enhance IL-2 secretion, stimulation of the ICOS pathway seems to enhance IL-10 secretion (Hutloff et al. 199. Nature 397:263). If a particular activity induced upon costimulation, e.g., T cell proliferation, cannot be inhibited by addition of blocking antibodies to known cytokines, the activity may result from the action of an unknown cytokine. Following costimulation, this cytokine could be purified from the media by conventional methods and its activity measured by its ability to induce T cell proliferation.

To identify cytokines which may prevent the induction of tolerance, an in vitro T cell costimulation assay as described above can be used. In this case, T cells would be given the primary activation signal and contacted with a selected cytokine, but would not be given the costimulatory signal. After washing and resting the T cells, the cells would be rechallenged with both a primary activation signal and a costimulatory signal. If the T cells do not respond (e.g., proliferate or produce cytokines) they have become tolerized and the cytokine has not prevented the induction of tolerance. However, if the T cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases. For example, one could administer a B7-4 blocking reagent together with a cytokine blocking antibody to a subject.

C. Identification of Molecules which Influence Costimulation

Another application of the peptide having the activity of a novel B lymphocyte antigen of the invention is the use of one or more of these peptides in screening assays to discover as yet undefined molecules which are modulators of costimulatory ligand binding and/or of intracellular signaling through T cells following costimulation. For example, a solid-phase binding assay using a peptide having the activity of a B7-4 molecule, could be used to identify molecules to which B7-4 binds and/or which inhibit binding of the antigen with an appropriate T cell ligand (e.g., CD28, CTLA4, or ICOS). In addition, an in vitro T cell costimulation assay as described above could be used to identify molecules which interfere with intracellular signaling through the T cells following costimulation as determined by the ability of these molecules to inhibit T cell proliferation and/or cytokine production (yet which do not prevent binding of a B7-4 molecule to its ligand). For example, the compound cyclosporine A inhibits T cell activation through stimulation via the T cell receptor pathway but not via the CD28/CTLA4 pathway. Therefore, a different intracellular signaling pathway is involved in costimulation. Molecules which interfere with intracellular signaling via the CD28/CTLA4 pathway may be effective as immunosuppressive agents in vivo (similar to the effects of cyclosporine A).

D. Identification of Molecules which Modulate Expression of a B7-4 Polypeptide

The antibodies produced using the proteins and peptides of the current invention can be used in a screening assay for molecules which modulate the expression of B7-4 polypeptide on cells. For example, molecules which effect intracellular signaling which leads to induction of expression B7-4 polypeptides e.g., in response to activation signals, can be identified by assaying expression of one or more B7-4 polypeptides on the cell surface. Reduced immunofluorescent staining by an anti-B7-4 or BB-1 antibody in the presence of the molecule would indicate that the molecule inhibits intracellular signals. Molecules which upregulate B7-4 polypeptide expression result in an increased immunofluorescent staining. Alternatively, the effect of a molecule on expression of a B7-4 polypeptide can be determined by detecting cellular B7-4 mRNA levels using a probe of the invention. For example, a cell which expresses a B7-4 polypeptide can be contacted with a molecule to be tested, and an increase or decrease in B7-4 mRNA levels in the cell detected by standard technique, such as Northern hybridization analysis or conventional dot blot of mRNA or total poly($A^+$)RNAs using a B7-4 cDNA probe labeled with a detectable marker. Molecules which modulate expression of a B7-4 polypeptide may be useful therapeutically for either upregulating or downregulating immune responses alone or in conjunction with soluble blocking or stimulating reagents. For instance, a molecule which inhibits expression of B7-4 could be administered together with a B7-4 blocking reagent for immunosuppressive purposes. Molecules which can be tested in the above-described assays include cytokines such as IL-4, γINF, IL-10, IL-12, GM-CSF and prostagladins.

E. Screening Assays:

The invention provides a method (also referred to herein as a "screening assay") for identifying modulators, i.e., candidate or test compounds or agents (e.g., peptides, peptidomimetics, small molecules or other drugs) which bind to B7-4 proteins, have a stimulatory or inhibitory effect on, for example, B7-4 expression or B7-4 activity.

In one embodiment, the invention provides assays for screening candidate or test compounds which bind to or modulate the activity of a B7-4 protein or polypeptide or biologically active portion thereof, e.g., modulate the ability of B7-4 polypeptide to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In another embodiment, an assay is a cell-based assay comprising contacting a cell expressing a B7-4 target molecule (e.g., a B7-4 ligand or intracellular interactor molecule phosphorylation substrate) with a test compound and determining the ability of the test compound to modulate (e.g. stimulate or inhibit) the activity of the B7-4 target molecule. Determining the ability of the test compound to modulate the activity of a B7-4 target molecule can be accomplished, for example, by determining the ability of the B7-4 protein to bind to or interact with the B7-4 target molecule or its ligand. Determining the ability of the B7-4 protein to bind to or interact with a ligand of a B7-4 molecule can be accomplished, e.g., by direct binding.

In a direct binding assay, the B7-4 protein could be coupled with a radioisotope or enzymatic label such that binding of the B7-4 protein to a B7-4 target molecule can be determined by detecting the labeled B7-4 protein in a complex. For example, B7-4 molecules, e.g., B7-4 proteins, can be labeled with $^{125}I$, $^{35}S$, $^{14}C$, or $^{3}H$, either directly or indirectly, and the radioisotope detected by direct counting of radioemmission or by scintillation counting. Alternatively, B7-4 molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between B7-4 and its target molecule, without the labeling of any of the interactants. For example, a microphysiometer can be used to detect the interaction of B7-4 with its target molecule without the labeling of either B7-4 or the target molecule. McConnell, H. M. et al. (1992) *Science* 257: 1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the B7-4 protein to bind to or interact with a B7-4 target molecule can be accomplished by determining the activity of the target molecule. For example, the activity of the target molecule can be determined by detecting induction of a cellular second messenger of the target (e.g., tyrosine kinase activity in a T cell), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response. For example, determining the ability of the B7-4 protein to bind to or interact with a B7-4 target molecule can be accomplished, for example, by measuring the ability of a compound to downmodulate T cell costimulation in a proliferation assay, or by interfering with the ability of a B7-4 polypeptide to bind to antibodies that recognize a portion of the B7-4 polypeptide.

In yet another embodiment, an assay of the present invention is a cell-free assay in which a B7-4 protein or biologically active portion thereof is contacted with a test compound and the ability of the test compound to bind to the B7-4 protein or biologically active portion thereof is determined. Binding of the test compound to the B7-4 protein can be determined either directly or indirectly as described above. In a preferred embodiment, the assay includes contacting the B7-4 protein or biologically active portion thereof with a known compound which binds B7-4 to form an assay mixture, contacting the assay mixture with a test compound, and determining the ability of the test compound to interact with a B7-4 protein, wherein determining the ability of the test compound to interact with a B7-4 protein comprises determining the ability of the test compound to preferentially bind to B7-4 polypeptide or biologically active portion thereof as compared to the known compound.

In another embodiment, the assay is a cell-free assay in which a B7-4 protein or biologically active portion thereof is contacted with a test compound and the ability of the test compound to modulate (e.g., stimulate or inhibit) the activity of the B7-4 protein or biologically active portion thereof is determined. Determining the ability of the test compound to modulate the activity of a B7-4 protein can be accomplished, for example, by determining the ability of the B7-4 protein to bind to a B7-4 target molecule by one of the methods described above for determining direct binding. Determining the ability of the B7-4 protein to bind to a B7-4 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a B7-4 protein can be accomplished by determining the ability of the B7-4 protein to further modulate the activity of a B7-4 target molecule (e.g., a B7-4 mediated signal transduction pathway component). For example, the activity of the effector molecule on an appropriate target can be determined, or the binding of the effector to an appropriate target can be determined as previously described.

In yet another embodiment, the cell-free assay involves contacting a B7-4 protein or biologically active portion thereof with a known compound which binds the B7-4 protein to form an assay mixture, contacting the assay mixture with a test compound, and determining the ability of the test compound to interact with the B7-4 protein, wherein determining the ability of the test compound to interact with the B7-4 protein comprises determining the ability of the B7-4 protein to preferentially bind to or modulate the activity of a B7-4 target molecule.

The cell-free assays of the present invention are amenable to use of both soluble and/or membrane-bound forms of proteins (e.g., B7-4 proteins or biologically active portions thereof, or receptors to which B7-4 binds). In the case of cell-free assays in which a membrane-bound form a protein is used (e.g., a cell surface B7-4 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON® X-100, TRITON® X-114, THESIT®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either B7-4 or its target molecule to facilitate separation of complexed from uncomplexed forms of one or both of the proteins, as well as to accommodate automation of the assay. Binding of a test compound to a B7-4 protein, or interaction of a B7-4 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/B7-4 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or B7-4 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of B7-4 binding or activity determined using standard techniques.

Other techniques for immobilizing proteins on matrices can also be used in the screening assays of the invention. For example, either a B7-4 protein or a B7-4 target molecule can be immobilized utilizing conjugation of biotin and streptavidin. Biotinylated B7-4 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with B7-4 protein or target molecules but which do not interfere with binding of the B7-4 protein to its target molecule can be derivatized to the wells of the plate, and unbound target or B7-4 protein trapped in the wells by antibody conjugation. Methods for detecting such complexes, in addition to those described above for the GST-immobilized complexes, include immunodetection of complexes using antibodies reactive with the B7-4 protein or target molecule, as well as enzyme-linked assays which rely on detecting an enzymatic activity associated with the B7-4 protein or target molecule.

In another embodiment, modulators of B7-4 expression are identified in a method wherein a cell is contacted with a candidate compound and the expression of B7-4 mRNA or protein in the cell is determined. The level of expression of B7-4 mRNA or protein in the presence of the candidate compound is compared to the level of expression of B7-4 mRNA or protein in the absence of the candidate compound. The candidate compound can then be identified as a modulator of B7-4 expression based on this comparison. For example, when expression of B7-4 mRNA or protein is greater (e.g., statistically significantly greater) in the presence of the candidate compound than in its absence, the candidate compound is identified as a stimulator of B7-4 mRNA or protein expression. Alternatively, when expression of B7-4 mRNA or protein is less (e.g., statistically significantly less) in the presence of the candidate compound than in its absence, the candidate compound is identified as an inhibitor of B7-4 mRNA or protein expression. The level of B7-4 mRNA or protein expression in the cells can be determined by methods described herein for detecting B7-4 mRNA or protein.

In yet another aspect of the invention, the B7-4 proteins, preferably a B7-4M membrane bound form, can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268: 12046–12054; Bartel et al. (1993) *Biotechniques* 14:920–924; Iwabuchi et al. (1993) *Oncogene* 8:1693–1696; and Brent WO94/10300), to identify other proteins, which bind to or interact with B7-4 ("B7-4-binding proteins" or "B7-4-bp") and are involved in B7-4 activity. Such B7-4-binding proteins are also likely to be involved in the propagation of signals by the B7-4 proteins or B7-4 targets as, for example, downstream elements of a B7-4-mediated signaling pathway. Alternatively, such B7-4-binding proteins may be B7-4 inhibitors.

The two-hybrid system is based on the modular nature of most transcription factors, which consist of separable DNA-binding and activation domains. Briefly, the assay utilizes two different DNA constructs. In one construct, the gene that codes for a B7-4 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a B7-4-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the B7-4 protein.

This invention further pertains to novel agents identified by the above-described screening assays. Accordingly, it is within the scope of this invention to further use an agent identified as described herein in an appropriate animal model. For example, an agent identified as described herein (e.g., a B7-4 modulating agent, an antisense B7-4 nucleic acid molecule, a B7-4-specific antibody, or a B7-4-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

F. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of B7-4 nucleotide sequences, described herein, can be used to map the location of B7-4 genes on a chromosome. The mapping of B7-4 sequences to chromosomes is an important first step in correlating these sequences with genes associated with disease.

Briefly, B7-4 genes can be mapped to chromosomes by preparing PCR primers (preferably 15–25 bp in length) from B7-4 nucleotide sequences. Computer analysis of B7-4 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to B7-4 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) Science 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using B7-4 nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) Proc. Natl. Acad. Sci. USA, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the B7-4 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The B7-4 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult.

The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the B7-4 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The B7-4 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or 3, can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from B7-4 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial B7-4 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique.

Examples of polynucleotide reagents include the B7-4 nucleotide sequences or portions thereof having a length of at least 20 bases, preferably at least 30 bases.

The B7-4 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such B7-4 probes can be used to identify tissue by species and/or by organ type.

In a similar fashion, these reagents, e.g., B7-4 primers or probes can be used to screen tissue culture for contamination (i.e. screen for the presence of a mixture of different types of cells in a culture).

G. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining B7-4 protein and/or nucleic acid expression as well as B7-4 activity, in the context of a biological sample (e.g., blood, serum, cells, tissue) to thereby determine whether an individual is afflicted with a disease or disorder, or is at risk of developing a disorder, associated with aberrant B7-4 expression or activity. The invention also provides for prognostic (or predictive) assays for determining whether an individual is at risk of developing a disorder associated with B7-4 protein, nucleic acid expression or activity. For example, mutations in a B7-4 gene can be assayed in a biological sample. Such assays can be used for prognostic or predictive purpose to thereby prophylactically treat an individual prior to the onset of a disorder characterized by or associated with B7-4 protein, nucleic acid expression or activity.

Another aspect of the invention pertains to monitoring the influence of agents (e.g., drugs, compounds) on the expression or activity of B7-4 in clinical trials.

These and other agents are described in further detail in the following sections.

1. Diagnostic Assays

An exemplary method for detecting the presence or absence of B7-4 protein or nucleic acid in a biological sample involves obtaining a biological sample from a test subject and contacting the biological sample with a compound or an agent capable of detecting B7-4 protein or nucleic acid (e.g., mRNA, genomic DNA) that encodes B7-4 protein such that the presence of B7-4 protein or nucleic acid is detected in the biological sample. A preferred agent for detecting B7-4 mRNA or genomic DNA is a labeled nucleic acid probe capable of hybridizing to B7-4 mRNA or genomic DNA. The nucleic acid probe can be, for example, a human B7-4 nucleic acid, such as the nucleic acid of SEQ ID NO:1 or 3, or a portion thereof, such as an oligonucleotide of at least 15, 30, 50, 100, 250 or 500 nucleotides in length and sufficient to specifically hybridize under stringent conditions to B7-4 mRNA or genomic DNA. Other suitable probes for use in the diagnostic assays of the invention are described herein.

A preferred agent for detecting B7-4 protein is an antibody capable of binding to B7-4 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect B7-4 mRNA, protein, or genomic DNA in a biological sample in vitro as well as in vivo. For example, in vitro techniques for detection of B7-4 mRNA include Northern hybridizations and in situ hybridizations. In vitro techniques for detection of B7-4 protein include enzyme linked immunosorbent assays (ELISAs), Western blots, immunoprecipitations and immunofluorescence. In vitro techniques for detection of B7-4 genomic DNA include Southern hybridizations. Furthermore, in vivo techniques for detection of B7-4 protein include introducing into a subject a labeled anti-B7-4 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting B7-4 protein, mRNA, or genomic DNA, such that the presence of B7-4 protein, mRNA or genomic DNA is detected in the biological sample, and comparing the presence of B7-4 protein, mRNA or genomic DNA in the control sample with the presence of B7-4 protein, mRNA or genomic DNA in the test sample.

The invention also encompasses kits for detecting the presence of B7-4 in a biological sample. For example, the kit can comprise a labeled compound or agent capable of detecting B7-4 protein or mRNA in a biological sample; means for determining the amount of B7-4 in the sample; and means for comparing the amount of B7-4 in the sample with a standard. The compound or agent can be packaged in a suitable container. The kit can further comprise instructions for using the kit to detect B7-4 protein or nucleic acid.

2. Prognostic Assays

The diagnostic methods described herein can furthermore be utilized to identify subjects having or at risk of developing a disease or disorder associated with aberrant B7-4 expression or activity. For example, the assays described herein, such as the preceding diagnostic assays or the following assays, can be utilized to identify a subject having or at risk of developing a disorder associated with B7-4 protein, nucleic acid expression or activity. Thus, the present invention provides a method for identifying a disease or disorder associated with aberrant B7-4 expression or activity in which a test sample is obtained from a subject and B7-4 protein or nucleic acid (e.g., mRNA, genomic DNA) is detected, wherein the presence of B7-4 protein or nucleic acid is diagnostic for a subject having or at risk of developing a disease or disorder associated with aberrant B7-4 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant B7-4 expression or activity. Thus, the present invention provides methods for determining whether a subject can be effectively treated with an agent for a disorder associated with aberrant B7-4 expression or activity in which a test sample is obtained and B7-4 protein or nucleic acid expression or activity is detected (e.g., wherein the abundance of B7-4 protein or nucleic acid expression or activity is diagnostic for a subject that can be administered the agent to treat a disorder associated with aberrant B7-4 expression or activity).

The methods of the invention can also be used to detect genetic alterations in a B7-4 gene, thereby determining if a subject with the altered gene is at risk for a disorder associated with the B7-4 gene. In preferred embodiments, the methods include detecting, in a sample of cells from the subject, the presence or absence of a genetic alteration characterized by at least one of an alteration affecting the integrity of a gene encoding a B7-4-protein, or the misexpression of the B7-4 gene. For example, such genetic alterations can be detected by ascertaining the existence of at least one of 1) a deletion of one or more nucleotides from a B7-4 gene; 2) an addition of one or more nucleotides to a B7-4 gene; 3) a substitution of one or more nucleotides of a B7-4 gene, 4) a chromosomal rearrangement of a B7-4 gene; 5) an alteration in the level of a messenger RNA transcript of a B7-4 gene, 6) aberrant modification of a B7-4 gene, such as of the methylation pattern of the genomic DNA, 7) the presence of a non-wild type splicing pattern of a messenger RNA transcript of a B7-4 gene, 8) a non-wild type level of a B7-4-protein, 9) allelic loss of a B7-4 gene, and 10) inappropriate post-translational modification of a B7-4-protein. As described herein, there are a large number of assay techniques known in the art which can be used for detecting alterations in a B7-4 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the B7-4-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a B7-4 gene under conditions such that hybridization and amplification of the B7-4-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl.*

Acad. Sci. USA 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a B7-4 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in B7-4 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in B7-4 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the B7-4 gene and detect mutations by comparing the sequence of the sample B7-4 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the B7-4 gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes formed by hybridizing (labeled) RNA or DNA containing the wild-type B7-4 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in B7-4 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a B7-4 sequence, e.g., a wild-type B7-4 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in B7-4 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat Res* 285:125–144; and Hayashi (1992) Genet Anal Tech Appl 9:73–79). Single-stranded DNA fragments of sample and control B7-4 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a B7-4 gene.

Furthermore, any cell type or tissue in which B7-4 is expressed may be utilized in the prognostic assays described herein.

VII. Administration of B7-4 Modulating Agents

B7-4 modulating agents of the invention are administered to subjects in a biologically compatible form suitable for pharmaceutical administration in vivo to either enhance or suppress T cell mediated immune response. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a B7-4 polypeptide may vary according to factors such as the disease state, age, sex, and weight of the individual, and the ability of peptide to elicit a desired response in the individual. Dosage regima may be adjusted to provide the optimum therapeutic response. For example, several divided doses may be administered daily or the dose may be proportionally reduced as indicated by the exigencies of the therapeutic situation.

The B7-4 modulating agent (e.g., a peptide, a nucleic acid molecule, or an antibody) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound. For example, to administer B7-4 modulating agent by other than parenteral administration, it may be necessary to coat the peptide with, or co-administer the peptide with, a material to prevent its inactivation.

A B7-4 modulating agent may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., a B7-4 polypeptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In one embodiment of the present invention a therapeutically effective amount of an antibody to a B7-4 protein is administered to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Monitoring the influence of agents (e.g., drugs or compounds) on the expression or activity of a B7-4 protein can be applied not only in basic drug screening, but also in clinical trials. For example, the effectiveness of an agent determined by a screening assay as described herein to increase B7-4 gene expression, protein levels, or upregulate B7-4 activity, can be monitored in clinical trials of subjects exhibiting decreased B7-4 gene expression, protein levels, or downregulated B7-4 activity. Alternatively, the effectiveness of an agent determined by a screening assay to decrease B7-4 gene expression, protein levels, or downregulate B7-4 activity, can be monitored in clinical trials of subjects exhibiting increased B7-4 gene expression, protein levels, or upregulated B7-4 activity. In such clinical trials, the expression or activity of a B7-4 gene, and preferably, other genes that have been implicated in a disorder can be used as a "read out" or markers of the phenotype of a particular cell.

For example, and not by way of limitation, genes, including B7-4, that are modulated in cells by treatment with an agent (e.g., compound, drug or small molecule) which modulates B7-4 activity (e.g., identified in a screening assay as described herein) can be identified. Thus, to study the effect of agents on a B7-4 associated disorder, for example, in a clinical trial, cells can be isolated and RNA prepared and analyzed for the levels of expression of B7-4 and other genes implicated in the B7-4 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of B7-4 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a B7-4 protein, mRNA, or genomic DNA in the pre-administration sample; (iii) obtaining one or more post-administration samples from the subject; (iv) detecting the level of expression or activity of the B7-4 protein, mRNA, or genomic DNA in the post-administration samples; (v) comparing the level of expression or activity of the B7-4 protein, mRNA, or genomic DNA in the pre-administration sample with the B7-4 protein, mRNA, or genomic DNA in the post administration sample or samples; and (vi) altering the administration of the agent to the subject accordingly. For example, increased administration of the agent may be desirable to increase the expression or activity of B7-4 to higher levels than detected, i.e., to increase the effectiveness of the agent. Alternatively, decreased administration of the agent may be desirable to decrease expression or activity of B7-4 to lower levels than detected, i.e. to decrease the effectiveness of the agent. According to such an embodiment, B7-4 expression or activity may be used as an indicator of the effectiveness of an agent, even in the absence of an observable phenotypic response.

This invention is further illustrated by the following examples which should not be construed as limiting. The contents of all references, patents and published patent applications cited throughout this application, as well as the Figures and the Sequence Listing are incorporated herein by reference.

EXAMPLES

Example 1

Isolation of B7-4 cDNA Molecules

The protein sequence of the extracellular domain of human B7-1 was used to search the public databases for nucleic acid molecules encoding homologous polypeptides. Two overlapping sequences in the EST database, AA292201 and AA399416, were identified. These sequences were used to isolate full-length B7-4 cDNAs from human activated keratinocyte and placental cDNA libraries as follows.

Oligonucleotides with the sequence CAGCTATGGTG-GTGCCGACTACAA (SEQ ID NO: 5) and AGGT-GCTAGGGGACAGTGTTAGACA (SEQ ID NO: 6) from these ESTs were synthesized. These oligonucleotides were used to prime a PCR reaction using as template cDNA prepared by reverse transcription of mRNAs from the spleen of a case of follicular lymphoma, activated B cells, INF-γ activated keratinocytes, normal spleen, and placenta. Conditions were 94° C., 1 min; 94° C., 30 sec, 56° C., 30 sec, 68° C., 1 min for 35 cycles; 68° C., 3 min, hold 4° C. All templates gave a band of the expected size of 389 bp. The 389 bp product from the PCR of TNF-γ activated keratinocytes was purified by agarose gel electrophoresis and 0.12 ng was used as a template in a PCR reaction containing 0.05 mM biotin-21-dUTP and the above primers. Conditions were 94° C., 1 min; 94° C., 30 sec, 56° C., 30 sec, 68° C., 2 min for 20 cycles; 68° C., 5 min, hold 4° C. The biotinylated PCR product was purified on a Nucleospin column (Clontech) and used as a probe in the ClonCapture cDNA selection procedure (Clontech). 60 ng of denatured, biotinylated PCR product was incubated with 2 mM $CoCl_2$, 1×RecA buffer, 1 µg of RecA protein, 1×ATP in a final volume of 30 µl. The reaction was incubated at 37° for 15 min. 0.7 µg of plasmid DNA of an activated keratinocyte cDNA library and 0.4 µg of a human placental cDNA library was added and incubation continued for 20 min. 50 ng of EcoRV digested lambda DNA was added to the reaction and incubated 5 min. 0.6 µl of 10% SDS and 5.6 µg of proteinase K were added and incubated at 37° for 10 min. Proteinase K was inactivated by adding 1 µl of 0.1 M PMSF. Streptavidin magnetic beads were preincubated with 5 µg of sheared salmon sperm DNA for 10 min and the beads captured with a magnet, the supernatant removed, and the beads resuspended in 30 µl of binding buffer (1 mM EDTA, 1 M NaCl, 10 mM Tris-HCl, pH 7.5). The beads were added to the reaction and the reaction incubated for 30 min at room temperature with gentle mixing. The beads were captured with a magnet and the supernatant removed. The beads were washed with 1 ml of washing buffer (1 mM EDTA, 2 M NaCl, 10 mM Tris-HCl, pH 7.5), beads were captured with a magnet and the supernatant removed. The wash procedure was repeated 3 times. One ml of sterile $H_2O$ was added to the washed beads, incubated 5 min at 37°, beads were captured on a magnet and the supernatant removed. Captured DNA was eluted by adding 0.1 ml of elution buffer (1 mM EDTA, 0.1 N NaOH), incubating 5 min at room temperature, beads were captured with a magnet and the supernatant removed and saved in a new tube. 22.5 µl of precipitation mix containing carrier and pH neutralizers was added along with 2.5 volumes of ethanol. The plasmid DNA was concentrated by centrifugation and re-dissolved in $H_2O$. Plasmid DNA was re-introduced into *E. coli* DH10B/P3 by electroporation and selected on LB-agar plates containing 7.5 µg/ml tetracycline and 25 µg/ml ampicillin. Colonies were lifted onto Nytran filters and hybridized with $^{32}$P-labeled oligonucleotides with the sequence CAGCTATG-GTGGTGCCGACTACAA (SEQ ID NO: 5), AGGT-GCTAGGGGACAGTGTTAGACA (SEQ ID NO: 6), and TCGCTTGTAGTCGGCACCACCATA (SEQ ID NO: 9). All oligos are from AA292201 sequence. Final wash conditions were 2×SSC, 0.1% SDS at 55° C. for 20 min. The two hybridizing colonies were picked and the sequence of the cDNA inserts was determined.

Sequencing revealed two forms of B7-4 molecules. The first form, B7-4 secreted (B7-4S) encodes a protein having a short hydrophilic domain without a membrane anchor. The nucleotide and amino acid sequences of this form are shown in SEQ ID NO:1 and 2, respectively. The second form, B7-4 membrane (B7-4M) encodes a protein having a transmembrane and short cytoplasmic domain. The nucleotide and amino acid sequences of this form are shown in SEQ ID NO:3 and 4, respectively. Both members of the B7-4 family identified have signal, IgV, and IgC domains, as illustrated in FIGS. 3 and 4. The B7-4M form has approximately 21% amino acid identity to human B7-1 and about 20% amino acid identity to human B7-2 as calculated using the default Blosum62 matrix with gap penalties set at existence 11 and extension 1 (See the NCBI website), under conditions where B7-1 and B7-2 have about 26% identity.

Example 2

Expression of B7-4 mRNA

An mRNA of the soluble form of B7-4 is predicted to be about 1.2 kb, though other sizes are possible. The mRNA of the second form is about 3.8 kb, with minor mRNAs of 1.6 and 6.5 kb.

Expression of B7-4 mRNA was analyzed. RNA was prepared by guanidine thiocyanate homogenization and cesium chloride centrifugation. Equal amounts of RNA (approximately 2 µg poly(A)+ RNA) were electrophoresed on an agarose gel, blotted, and hybridized to a portion of $^{32}$P-labeled B7-4 cDNA common to both the B7-4S and B7-4 M forms. These B7-4 mRNAs are highly expressed in placenta, lung, and heart and are moderately expressed in the thymus. In addition, these B7-4 polypeptides are weakly expressed in skeletal muscle, kidney, pancreas, prostate, testis, ovary, small intestine, colon, and peripheral blood leukocytes. They were also found to be very weakly expressed in liver or brain. B7-4 mRNAs were not expressed in unstimulated monocytes, but were strongly induced by IFN-γ. Similarly, the expression of these mRNAs was found to be induced in keratinocytes by TPA/IFN-γ and in dendritic cells by IFN-γ. These B7-4 mRNAs were not expressed in unstimulated B cells, but were induced by Ig crosslinking.

Expression of these B7-4 mRNAs was also examined in a variety of cell lines. They were not found to be expressed in B cell lines such as Raji, Ramos, LBL, Nalm 6, and DHL-4. They were also not expressed in T cell lines, such as Jurkat, Rex, CEM, HPB-ALL, Peer4, and H9 or in HTLV-1 transformed T cell lines such as SPP and MT2 or in the myeloid line U937.

Example 3

Binding of B7-4 Molecules to T Cell Ligands or Antibodies

COS cells were transfected with either vector DNA (pCD-NAI), or an expression plasmid containing the B7-4M cDNA. After 72 hours, the tansfected COS cells were detached by incubation in PBS containing 0.5 mM EDTA for 30 min. at 37° C.

Figure 9:
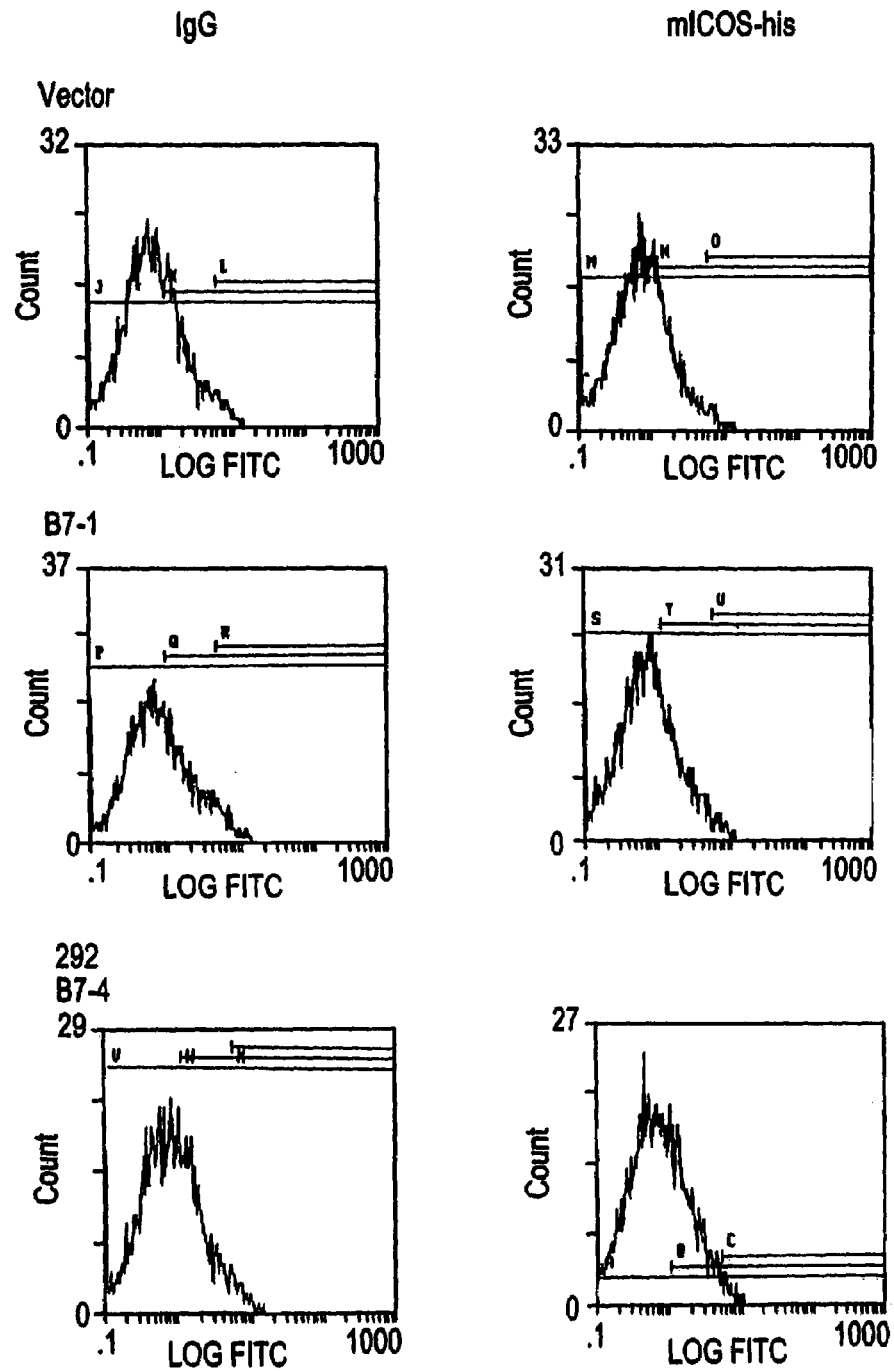
FIG. 9 illustrates the results FACS analysis of binding of IgG and murine ICOS-his fusion protein by B7-4M-transfected COS cells.
Figure 10:
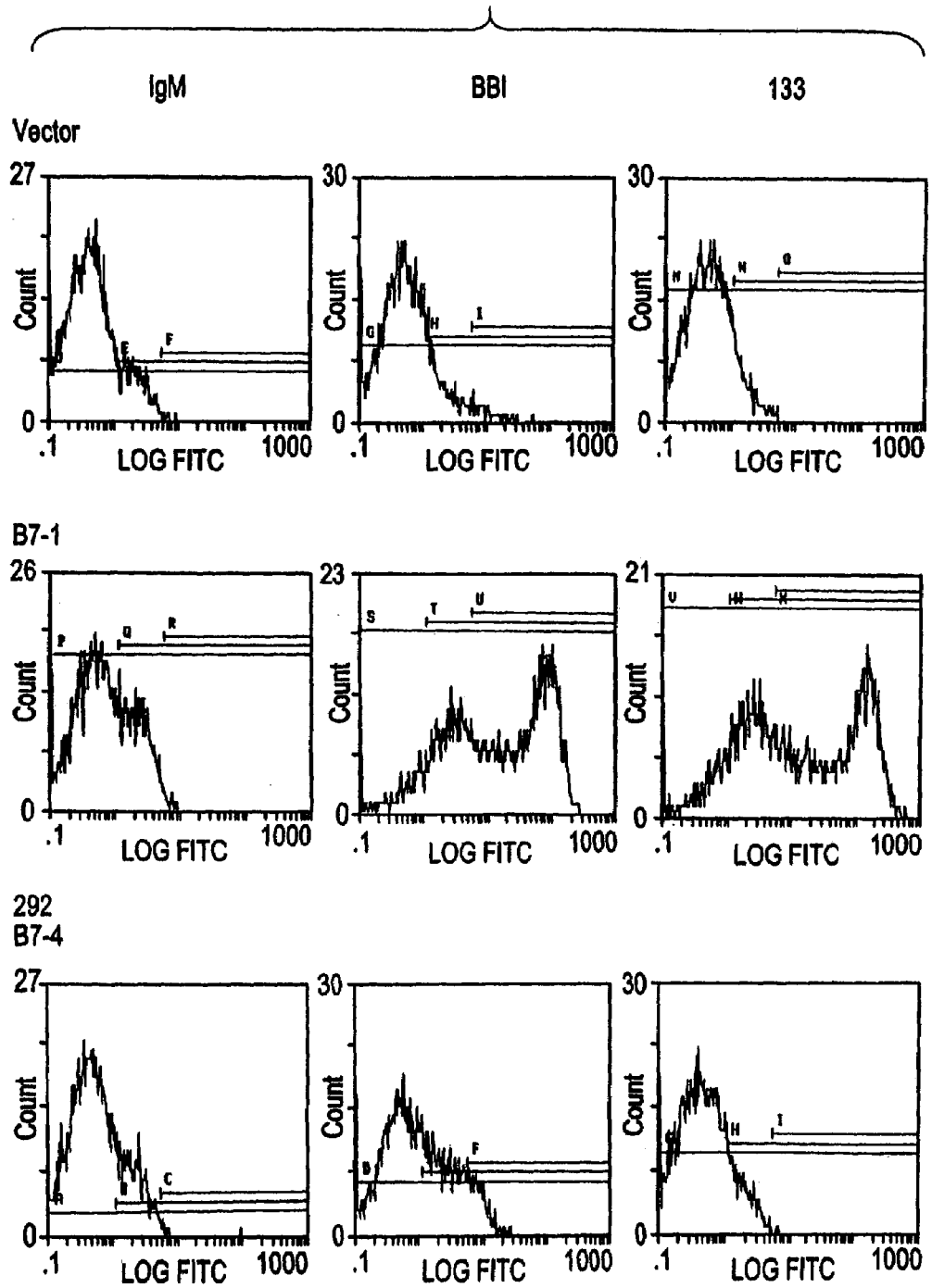
FIG. 10 illustrates the results FACS analysis of binding of IgM, BB1 and 133 antibodies to B7-4M-transfected COS cells.

The ability of COS cells expressing B7-4M to bind to various T cell ligands and antibodies was tested. FACS analysis of binding of CD28Ig, CTLA4-Ig, and control Ig by B7-4-transfected COS cells showed that neither CD28Ig nor CTLA4-Ig was bound by B7-4 (FIG. 8). The ability of COS cells expressing B7-4M to bind to IgG and murine ICOS-his fusion protein was also tested. No binding of human B7-4 to murine ICOS was detected (FIG. 9). As shown in FIG. 10, FACS analysis revealed binding of BB1 (anti B7-1 and anti B7-3), but not IgM or 133 (anti-B7) antibodies to B7-4-transfected COS cells (experiments shown employed unstable transfectants).

Example 4

Costimulation of T Cell Proliferation By B7-4 Molecules

The ability of B7-4 polypeptides to costimulate human T cell proliferation was tested.

Human CD28$^+$ T cells were isolated by immunomagnetic bead depletion using monoclonal antibodies directed against B cells, natural killer cells and macrophages as previously described (Gimmi, C. D., et al. (1993) *Proc. Natl. Acad. Sci. USA* 90, 6586–6590). B7-4 and vector transfected COS cells were harvested 72 hours after transfection, incubated with 25 µg/ml of mitomycin-C for 1 hour, and then extensively washed. $10^5$ naïve T Cells were stimulated with plate bound anti-CD3 mAb plus 20,000 mitomycin-c treated COS cells transfected with the indicated DNA construct.

T cell proliferation was measured by 3H-thymidine (1 µCi) incorporated for the last 12 hours of a 72 hour incubation. As shown in FIGS. 11 and 12, COS cells expressing B7-4 can costimulate T cell proliferation.

Example 5

Further Characterization of B7-4 mRNA Expression: Northern Blot Analysis

Mouse and human multiple tissue Northern blots (Clontech, Palo Alto, Calif.) were probed with $^{32}$P-dCTP radiolabeled cDNA probes in QuikHyb (Stratagene, La Jolla, Calif.) according to the manufacturer's instructions. The human B7-4 probe consisted of a 1 kb BamHI/NotI fragment of the cDNA spanning the coding region and 3' untranslated region of SEQ ID NO:1. The mouse B7-4 probe consisted of a 300 bp cDNA fragment from the coding region. Control actin probes were supplied by Clontech. Blots were washed twice at room temperature in 2×SSC, 0.1% SDS, followed by 0.2×SSC, 0.1% SDS at 65° C., and examined by autoradiography.

B7-4 mRNA was expressed at high levels in heart, human placenta, and human fetal liver, and at lower levels in spleen, lymph nodes, thymus, and mouse liver.

B7-4 mRNA was expressed in a variety of transformed mouse cell lines, including PU5-1.8, RAW 264.7, K-Balb, M-MSV-Balb/3T3, Hepa 1-6, R1.1, L1210, P38D1, P815, and NB41A3 cells.

Example 6

Further Characterization of B7-4 mRNA Expression

B7-4 mRNA expression on antigen presenting cells was examined and compared to the expression of B7-1 and B7-2 on those cells.

For RNA blot hybridization, the 1.6 kb human and 3.6 kb murine B7-4 cDNAs were excised by digestion with Xba I and labeled by random priming with γ-$^{32}$P-ATP and the Klenow fragment of DNA polymerase I. RNA blots were hybridized as described in Freeman, G. J. et al. (1992) *J. Immunol.* 149:3795–3801.

Human dendritic cells were derived from peripheral blood. Mononuclear cells were isolated after fractionation on a Ficoll gradient. Non-adherent cells were removed and the remaining cells cultured in 150 ng/ml human GM-CSF (R&D Systems) and 100 ng/ml human IL-4 (R&D Systems) for 2 days. The non-adherent dendritic cells were isolated (CD80$^+$ CD86$^+$ HLA-DR$^+$ CD54$^+$ CD58$^+$ CD1a$^+$) and cultured in GM-CSF alone or activated with GM-CSF, 2.5 µg/ml LPS (Sigma Chemicals), and 10 ng/ml human Interferon-γ. At 4 hours and 20 hours after activation, cells were harvested and RNA isolated using the RNeasy kit (Qiagen).

Murine bone marrow mononuclear cells were immunodepleted of granulocytes, lymphocytes and Ia$^+$ cells by magnetic activated cell sorting and cultured in petri dishes with GM-CSF and IL-4. Dendritic cells were harvested as the non-adherent population after 7 days of culture, and demonstrated to be 75–80% CD11c$^+$, high IA$^+$ cells. Cells were activated with LPS and human interferon-γ.

Analysis of expression in human blood monocytes by RNA blot hybridization demonstrated that B7-2 is not expressed by unstimulated monocytes, but is rapidly upregulated upon interferon-γ treatment. Treatment of monocytes with another pro-inflammatory cytokine, tumor necrosis factor (TNF)-α led to a low level induction similar to that found with medium alone, presumably as a result of activation by adherence to plastic. In addition to the major 4.2 kb B7-4 mRNA, a minor 1.8 kb B7-4 mRNA species was also observed in interferon-γ treated monocytes. Expression of B7-4 by human B-cells activated by cell surface immunoglobulin cross-linking, but not by the Raji cell line, was also observed. Similarly, B7-1 is not expressed by unstimulated monocytes, but is upregulated in response to interferon-γ with kinetics similar to B7-4 expression. In contrast, B7-2 mRNA is constitutively expressed in monocytes and levels are unaffected by interferon-γ or TNF-α treatment.

The expression patterns of B7-1, B7-2, and B7-4 are distinct. B7-2, one of the ligands of CD28 and CTLA-4, is constitutively expressed on monocytes; however, constitutive expression of B7-1 and B7-2 is not seen in any organ. B7-1 and B7-2 expression can be induced in dendritic cell, macrophages and B cells (Boussiotis. 1996. Immunol. Rev. 153:5) as well as some types of fibroblast and epithelial cells. In contrast, B7-4 is expressed constitutively by non-lymphoid, parenchymal organs such as heart, placenta, skeletal muscle and lung, but not small intestine B7-4 is also expressed in some cancers.

In murine tissues, an approximately 3.7 kb B7-4 mRNA transcript was detected by northern blot hybridization. The distribution of the murine B7-4 mRNA closely resembled that of the human B7-4, with high levels in heart, thymus and lung, and low levels in kidney, spleen and liver.

Example 7

Chromosomal Localization of B7-4

The chromosomal localization of the B7-4 genes was determined using a monochromosomal blot kit commercially available from Quantum (Toronto, Canada). The blots were probed with a sequence that recognizes both B7-4S and B7-4M. Using this method, the B7-4 polypeptides have been localized to human chromosome 9, whereas B7-1 and B7-2 have been localized to human chromosome 3. The butyrophilins, which also share limited amino acid sequence identity with the B7-4 family have been localized to the major histocompatability complex on chromosome 6. The chromosomal localization of B7-4 was also confirmed by PCR. The chromosomal location of B7-4 was confirmed using B7-4 specific primers in PCR amplification of monochromosomal somatic cell hybrid DNA templates available from Quantum Technologies (Canada).

Example 8

Generation of Murine Antibodies to B7-4

Mammalian expression vectors (pEF6 or pcDNA3.1 (Invitrogen)) were prepared comprising murine and human B7-4 cDNA. The cDNA/vector construct was dissolved in 0.9% saline at 1 mg/ml (not TE or PBS).

Before immunization, 78 μl of 1 mg/ml cardiotoxin (Sigma #C-1777) in 0.9% saline was injected into the tibialis anterior muscle of each hind limb of the mouse being immunized. Each mouse was then left alone for 5 days.

After anesthetizing the mice, 50 μl of 1 mg/ml purified B7-4 cDNA/vector construct (in 0.9% saline) was injected into each regenerating tibialis anterior muscle.

Antibody titers were measured approximately six days after immunization using standard methods, for example, in an ELISA assay. The cDNA immunization was repeated every 2–4 weeks for three cycles (until the antibody titre was >1:10,000). Mice were then boosted with CHO cells transfected with B7-4.

Spleen cells isolated from mice having appropriate antibody titers were harvested. The spleen cells were fused to fusion partners (SP2-0) to make hybridomas. Hybridomas and antibodies were manipulated using standard methods (see, e.g., "Antibodies: A Laboratory Manual", Harlow, E. and Lane, D., Cold Spring Harbor Laboratory (1988), which is incorporated herein by reference).

Antibodies 2A3, 10D9, and 11D12 were selected in screening assays. These antibodies were found to bind to COS or CHO cells transfected with human B7-4 and not to mock transfected cells or to cells transfected with mouse B7-4. The antibodies were used to detect the presence of B7-4 on various cell populations. B7-4 expression was observed, inter alia, on heart tissue, tumor cells (including some lung tumor cells, some ovarian tumor cells, some breast tumor cells, some epithelial tumor cells, and some squamous cell carcinomas), placenta, and thymic epithelium.

Example 9

Generation of Fully Human Antibodies to B7-4

In this example, fully human antibodies against B7-4 are made in mice that are transgenic for human immunoglobulin framework genes. Transgenic mice are made using standard methods, e.g., according to Hogan, et al., "Manipulating the Mouse Embryo: A Laboratory Manual", Cold Spring Harbor Laboratory, which is incorporated herein by reference, or are purchased commercially. Embryonic stem cells are manipulated according to published procedures (Teratocarcinomas and embryonic stem cells: a practical approach, Robertson, E. J. ed., IRL Press, Washington, D.C., 1987; Zjilstra et al. (1989) *Nature* 342:435–438; and Schwartzberg et al. (1989) *Science* 246:799–803, each of which is incorporated herein by reference). DNA cloning procedures are carried out according to Sambrook, J. et al. in Molecular Cloning: A Laboratory Manual, 2d ed., 1989, Cold Spring Harbor Laboratory Press, Cold Spring Harbor, N.Y., which is incorporated herein by reference. Oligonucleotides are synthesized, e.g., on an Applied Bio Systems oligonucleotide synthesizer according to specifications provided by the manufacturer or are purchased commercially.

Transgenic mice are immunized using a purified or recombinant B7-4 or a fusion protein comprising at least an immunogenic portion of the extracellular domain of B7-4. Approximately four hundred μg of B7-4 in 100 μL of phosphate buffered saline (PBS) is injected intraperitoneally into each mouse. Serum samples are collected approximately six days later by retro-orbital sinus bleeding.

Antibody reactivity and specificity for B7-4 are assessed using an indirect enzyme-linked immunosorbent assay (ELISA). Several immunoglobulin superfamily molecules are tested as controls (e.g., CTLA4 and CD28) to analyze the antibody specificity of the antibody for B7-4. Antibodies having human framework regions which bind to PD-L2 are detected by enzyme conjugates specific for human IgM and human IgG sub-classes with no cross reactivity to mouse immunoglobulin. Briefly, PVC microtiter plates are coated with B7-4 by coating wells overnight at 37° C. with 5 μg/mL B7-4 in PBS. Serum samples are diluted in PBS, 5% serum, 0.5% Tween-20 and are incubated in the wells for 1 hour at room temperature, followed by anti-human IgG Fc and IgG F(ab')-horseradish peroxidase or anti-human IgM Fc-horseradish peroxidase in the same diluent. After 1 hour at room temperature enzyme activity is assessed by addition of ABTS substrate (Sigma, St. Louis, Mo.) and read after 30 minutes at 415–490 nm. In pre-immunization serum samples from the same mice, titers of human antibodies to the same target antigens are also tested.

Spleen cells isolated from mice having appropriate antibody titers are harvested. The spleen cells are fused to appropriate fusion partners (e.g., myeloma cells) to make hybridomas. Hybridomas and antibodies are manipulated according to "Antibodies: A Laboratory Manual", Ed Harlow and David Lane, Cold Spring Harbor Laboratory (1988), which is incorporated herein by reference.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. An isolated polypeptide comprising the amino acid sequence of SEQ ID NO:2 or 4.

2. The polypeptide of claim 1, further comprising heterologous amino acid sequences.

3. The polypeptide of claim 2, wherein the heterologous amino acid sequences are from an immunoglobulin molecule.

4. An isolated polypeptide comprising from about amino acid residue 19 to amino acid residue 245 of SEQ ID NO:2 or from about amino acid residue 19 to amino acid residue 238 of SEQ ID NO: 4.

5. An isolated polypeptide encoded by a nucleic acid molecule which hybridizes over its full-length under conditions of incubation at 45° C. in 6×sodium chloride/sodium citrate (SSC), followed by washing in 0.2×SSC, 0.1% SDS, at 50–65° C. to the complement of a nucleic acid molecule of SEQ ID NO: 1 or 3, wherein the polypeptide costimulates T cell proliferation in vitro when the polypeptide is present on a first surface and a molecule that transmits an activating signal via the T cell receptor is present on a second, different surface.

6. The polypeptide of claim 5, further comprising heterologous amino acid sequences.

7. The polypeptide of claim 6, wherein the heterologous amino acid sequences are from an immunoglobulin molecule.

8. An isolated polypeptide encoded by a nucleic acid molecule having a nucleotide sequence at least about 95% identical to the nucleotide sequence of SEQ ID NO: 1 or 3, wherein the polypeptide costimulates T cell proliferation in vitro when the polypeptide is present on a first surface and a molecule that transmits an activating signal via the T cell receptor is present on a second, different surface.

9. The polypeptide of claim 8, further comprising heterologous amino acid sequences.

10. The polypeptide of claim 9, wherein the heterologous amino acid sequences are from an immunoglobulin molecule.

11. An isolated polypeptide comprising an amino acid sequence at least about 95% identical to the amino acid sequence of SEQ ID NO: 2 or 4, wherein the polypeptide costimulates T cell proliferation in vitro when the polypeptide is present on a first surface and a molecule that transmits an activating signal via the T cell receptor is present on a second, different surface.

12. The polypeptide of claim 11, further comprising heterologous amino acid sequences.

13. The polypeptide of claim 12, wherein the heterologous amino acid sequences are derived from an immunoglobulin molecule.

14. An isolated polypeptide comprising from about amino acid residue 19 to amino acid residue 227 of SEQ ID NO: 4.

* * * * *

UNITED STATES PATENT AND TRADEMARK OFFICE
CERTIFICATE OF CORRECTION

| | | |
|---|---|---|
| PATENT NO. | : 7,038,013 B2 | Page 1 of 1 |
| APPLICATION NO. | : 10/002775 | |
| DATED | : May 2, 2006 | |
| INVENTOR(S) | : Gordon J. Freeman et al. | |

It is certified that error appears in the above-identified patent and that said Letters Patent is hereby corrected as shown below:

In the Specification

At column 1, line 14, under Government Funding should read:

--This invention was made with government support under AI039671, AI044690, CA084500 and AI041584 awarded by the National Institutes of Health. The government has certain rights in the invention.--

Signed and Sealed this
Eighth Day of September, 2015

Michelle K. Lee
*Director of the United States Patent and Trademark Office*